(12) United States Patent
Ronaghi et al.

(10) Patent No.: US 12,416,048 B2
(45) Date of Patent: Sep. 16, 2025

(54) NUCLEIC ACID SYNTHESIS TECHNIQUES

(71) Applicant: Illumina, Inc., San Diego, CA (US)

(72) Inventors: Mostafa Ronaghi, San Francisco, CA (US); Molly He, San Diego, CA (US); Cheng-yao Chen, San Diego, CA (US); Michael Previte, San Diego, CA (US); M. Shane Bowen, San Diego, CA (US)

(73) Assignee: Illumina, Inc., San Diego, CA (US)

( * ) Notice: Subject to any disclaimer, the term of this patent is extended or adjusted under 35 U.S.C. 154(b) by 1125 days.

(21) Appl. No.: 16/704,190

(22) Filed: Dec. 5, 2019

(65) Prior Publication Data

US 2020/0181699 A1 Jun. 11, 2020

Related U.S. Application Data

(63) Continuation of application No. 15/312,851, filed as application No. PCT/US2015/030889 on May 14, 2015, now Pat. No. 10,570,447.

(60) Provisional application No. 61/994,498, filed on May 16, 2014.

(51) Int. Cl.
*C12Q 1/6874* (2018.01)
*B01J 19/00* (2006.01)

(52) U.S. Cl.
CPC ........ *C12Q 1/6874* (2013.01); *B01J 19/0046* (2013.01); *B01J 2219/00587* (2013.01); *B01J 2219/00605* (2013.01); *B01J 2219/00689* (2013.01); *B01J 2219/00693* (2013.01); *B01J 2219/00695* (2013.01); *B01J 2219/00698* (2013.01); *B01J 2219/00704* (2013.01); *B01J 2219/00722* (2013.01)

(58) Field of Classification Search
CPC .. C12Q 1/6874; C12Q 1/6806; B01J 19/0046; B01J 2219/00587; B01J 2219/00605; B01J 2219/00689; B01J 2219/00693; B01J 2219/00695; B01J 2219/00698; B01J 2219/00704; B01J 2219/00722
See application file for complete search history.

(56) References Cited

U.S. PATENT DOCUMENTS

| | | | |
|---|---|---|---|
| 5,528,050 A | 6/1996 | Miller | |
| 5,641,658 A | 6/1997 | Adams | |
| 5,719,391 A | 2/1998 | Kain | |
| 5,871,921 A | 2/1999 | Landegren | |
| 6,124,120 A | 9/2000 | Lizardi | |
| 6,172,218 B1 | 1/2001 | Brenner | |
| 6,210,891 B1 | 4/2001 | Nyren | |
| 6,258,568 B1 | 7/2001 | Nyren | |
| 6,274,320 B1 | 8/2001 | Rothberg | |
| 6,306,597 B1 | 10/2001 | Macevicz | |
| 6,969,488 B2 | 11/2005 | Bridgham | |
| 7,057,026 B2 | 6/2006 | Barnes | |
| 7,071,324 B2 * | 7/2006 | Preparata | C12Q 1/6874 536/24.31 |
| 7,115,400 B1 | 10/2006 | Adessi | |
| 7,211,414 B2 | 5/2007 | Hardin | |
| 7,315,019 B2 | 1/2008 | Turner | |
| 7,329,492 B2 | 2/2008 | Hardin | |
| 7,405,281 B2 | 7/2008 | Xu | |
| 7,914,739 B2 | 3/2011 | Heiner | |
| 8,158,926 B2 | 4/2012 | Feng | |
| 8,241,573 B2 | 8/2012 | Banerjee | |
| 8,563,477 B2 | 10/2013 | Smith | |
| 2002/0055100 A1 * | 5/2002 | Kawashima | C12Q 1/6837 536/23.1 |
| 2004/0002090 A1 | 1/2004 | Mayer | |
| 2004/0096853 A1 | 5/2004 | Mayer | |
| 2004/0219063 A1 | 11/2004 | Heiner | |
| 2005/0100900 A1 | 5/2005 | Kawashima | |
| 2005/0227316 A1 | 10/2005 | Santi | |
| 2006/0188901 A1 | 8/2006 | Barnes | |
| 2006/0240439 A1 | 10/2006 | Smith | |
| 2006/0281109 A1 | 12/2006 | Barr Ost | |
| 2007/0031942 A1 | 2/2007 | Xialoian | |

(Continued)

FOREIGN PATENT DOCUMENTS

| | | |
|---|---|---|
| WO | WO 1991/06678 | 5/1991 |
| WO | WO 1997/20948 | 6/1997 |
| WO | WO 2004/018497 | 3/2004 |
| WO | WO 2005/065814 | 7/2005 |
| WO | WO 2006/064199 | 6/2006 |
| WO | WO 2007/010251 | 1/2007 |
| WO | WO 2007/060456 | 5/2007 |
| WO | WO 2007/123744 | 11/2007 |

(Continued)

OTHER PUBLICATIONS

Liu, Lin, et al. "A brief utilization report on the Illumina HiSeq 2000 sequencer." Mycology 2.3 (2011): 169-191. (Year: 2011).*

(Continued)

*Primary Examiner* — Anne M. Gussow
*Assistant Examiner* — Kyle T Rega
(74) *Attorney, Agent, or Firm* — Illumina, Inc.

(57) ABSTRACT

A method for synthesizing a nucleic acid includes synthesizing one or more nucleic acid fragments on a substrate. The synthesized one or more nucleic acid fragments may be amplified on the substrate. The method also includes sequencing the synthesized or amplified one or more nucleic acid fragments on the substrate. The sequencing may provide feedback to designs of the one or more nucleic acid fragments. The method further includes harvesting the synthesized or amplified one or more nucleic acid fragments based on sequencing. The synthesized or amplified one or more nucleic acid fragments may be assembled to generate a target nucleic acid.

20 Claims, 8 Drawing Sheets

(56) References Cited

U.S. PATENT DOCUMENTS

| | | | |
|---|---|---|---|
| 2007/0099208 A1 | 5/2007 | Drmanac | |
| 2007/0128624 A1 | 6/2007 | Gormley | |
| 2007/0166705 A1 | 7/2007 | Milton | |
| 2008/0009420 A1 | 1/2008 | Schroth | |
| 2008/0108082 A1 | 5/2008 | Rank | |
| 2010/0216648 A1 | 8/2010 | Staehler | |
| 2011/0059865 A1 | 3/2011 | Smith | |
| 2012/0122737 A1 | 5/2012 | Sabot | |
| 2012/0270305 A1 | 10/2012 | Reed | |
| 2012/0316086 A1 | 12/2012 | Shengrong | |
| 2013/0023422 A1 | 1/2013 | Feng | |
| 2013/0059296 A1 | 3/2013 | Jacobsen | |
| 2013/0079232 A1* | 3/2013 | Kain | C12Q 1/6869 435/6.1 |
| 2013/0260372 A1 | 10/2013 | Buermann | |
| 2014/0079923 A1 | 3/2014 | George | |

FOREIGN PATENT DOCUMENTS

| | | |
|---|---|---|
| WO | WO 2008/054543 | 5/2008 |
| WO | WO 2011/025477 | 3/2011 |
| WO | WO 2012/050920 | 4/2012 |
| WO | WO 2012/154201 | 11/2012 |

OTHER PUBLICATIONS

Schmidt, Wolfgang M., and Manfred W. Mueller. "Controlled ribonucleotide tailing of cDNA ends (CRTC) by terminal deoxynucleotidyl transferase: a new approach in PCR-mediated analysis of mRNA sequences." Nucleic acids research 24.9 (1996): 1789-1791. (Year: 1996).*

Boulé, Jean-Baptiste, François Rougeon, and Catherine Papanicolaou. "Terminal deoxynucleotidyl transferase indiscriminately incorporates ribonucleotides and deoxyribonucleotides." Journal of Biological Chemistry 276.33 (2001): 31388-31393 (Year: 2001).*

Singhal (Journal of Biological Chemistry 268.21 (1993): 15906-15911) (Year: 1993).*

Kim, et al, Shotgun DNA synthesis for the high-throughput construction of large DNA molecules, Nucleic Acids Research 40(18):e140 (2012).

Adessi et al., Solid phase DNA amplification: characterisation of primer attachment and amplification mechanisms, Nucl. Acids Res. 28:E87 (2000).

Bentley, et al. Accurate Whole Human Genome Sequencing using Reversible Terminator Chemistry, Nature 456:53-59 (2008).

Brenner et al., Gene expression analysis by massively parallel signature sequencing (MPSS) on microbead arrays Nat. Biotechnol. 18:630-634 (2000).

Brenner et al., In vitro cloning of complex mixtures of DNA on microbeads: Physical separation of differentially expressed cDNAs Proc. Natl. Acad. Sci. USA 97:1665-1670 (2000).

Dressman et al., Transforming single DNA molecules into fluorescent magnetic particles for detection and enumeration of genetic variations, Proc. Natl. Acad. Sci. USA 100:8817-8822 (2003).

Lizardi et al., Mutation detection and single-molecule counting using isothermal rolling-circle amplification, *Nat. Genet.* 19:225-232 (1998).

Mitra et al., Fluorescent in situ sequencing on polymerase colonies Anal. Biochem. 320:55-65 (2003).

Mitra et al., Digital genotyping and haplotyping with polymerase colonies, Proc. Natl. Acad. Sci. USA 100:5926-5931 (2003).

Pemov et al., DNA analysis with multiplex microarray-enhanced PCR, Nucl. Acids Res. 33:e11(2005).

Reinartz, et al., Massively parallel signature sequencing (MPSS) as a tool for in-depth quantitative gene expression profiling in all organisms, Brief Funct. Genomic Proteomic 1:95-104 (2002).

Ronaghi et al., Real-Time DNA Sequencing Using Detection of Pyrophosphate Release *Analytical Biochemistry* 242(1):84-89 (1996).

Ronaghi et al., A Sequencing Method Based on Real-Time Pyrophosphate, *Science* 281(5375):363-365 (1998).

Ronaghi, M. Pyrosequencing Sheds Light on DNA Sequencing, *Genome Res.* 11(1):3-11 (2001).

Mardis, et al., Next Generation DNA Sequencing Methods. Annual Review of Genomics and Human Genetics, 9:387-402 (2008).

\* cited by examiner

NUCLEIC ACID SYNTHESIS TECHNIQUES

RELATED APPLICATIONS

This application is a continuation of U.S. application Ser. No. 15/312,851 filed Nov. 21, 2016 which is the U.S. National Phase under 35 U.S.C. § 371 of Int. App. No. PCT/US2015/030889 entitled NUCLEIC ACID SYNTHESIS TECHNIQUES, filed May 14, 2015, designating the U.S.; which is based on, and claims the benefit of, U.S. Prov. App. No. 61/994,498, filed on May 16, 2014, the contents of which are each incorporated herein by reference in its entirety.

BACKGROUND

The invention relates generally to the field of nucleic acid synthesis and, more specifically, to methods and systems for synthesizing nucleic acids and quality control of such synthesis.

Recombinant nucleic acid techniques have facilitated the study of isolated genes in a wide range of organisms. For example, such techniques have allowed researchers to express a particular gene (e.g., a mouse gene) in a host organism (e.g., bacteria) to study not only the effects of the gene itself, but also to study its expression products. While such techniques have been used to study naturally-occurring nucleic acids, researchers have also been interested in studying the effects of particular mutations or changes in a nucleic acid sequence. For example, targeted mutations may be introduced into a nucleic acid sequence that in turn result in a change in an expressed protein sequence. Researchers may then study the effects of such mutations on protein interactions of interest. Such mutations may be introduced through PCR-based techniques and the resulting sequences may be expressed in host cells. However, these techniques may involve labor-intensive analysis and time-consuming host cell propagation to determine if a particular host cell has incorporated the sequence of interest. Further, while recombinant techniques may be suited for simply generating mutations (e.g. point mutations, deletions, or substitutions) of a pre-existing nucleic acid sequence, such techniques are not well suited to creating an entirely synthetic, template-independent nucleic acid molecule.

Some nucleic acid synthesis techniques are chemically-based or enzymatic techniques, e.g., chemical solid phase synthesis, that involve adding individual nucleotides to one another in the desired order to form a polynucleotide chain, such as a PCR primer of limited length (e.g., 30-50 nucleotides). However, nucleic acid synthesis techniques suitable for forming relatively short sequences may be slow and/or error-prone when used for synthesis of a long polynucleotide chain (e.g., greater than 50 nucleotides). For example, techniques with an error-rate of $1/500$ nucleotides may yield generally error-free short sequences of under 50 nucleotides, but may introduce several errors when used to synthesize sequences of 500-2000 nucleotides.

BRIEF DESCRIPTION

Provided herein are techniques for synthesizing nucleic acids with improved efficiency and accuracy. The disclosed techniques can incorporate quality feedback at one or more synthesis phases to facilitate selection of a nucleic acid molecule with a desired quality level (e.g., no errors in the nucleotide sequence or errors with a defined error range) from a group of synthesized molecules produced by a synthesis process that is suspected of generating errors. In certain embodiments, the nucleic acid synthesis techniques may incorporate a plurality of nucleic acid fragments that are designed, separately synthesized, and then assembled. In particular implementations, the quality feedback may be based on sequencing data obtained for the individual fragments and/or for the assembled nucleic acid molecule formed from the individual fragments. For example, a plurality of individual fragments may be synthesized and sequenced, with only the fragments having the correct sequence being collected for later assembly into a nucleic acid molecule. In cases where multiple copies of each fragment are separately synthesized, a correct copy can be collected while incorrect copies are avoided or even discarded. The assembled molecules may also be sequenced to select for molecules with a desired sequence error profile. Again, only assembled nucleic acid molecules having the desired sequence may be harvested.

In another embodiment, the fragments may be synthesized and assembled without sequencing the individual fragments prior to assembly. Here, quality control may be provided via sequencing information for the assembled molecules. However, even in such an embodiment, other quality control steps may be implemented. For example, each individual fragment synthesis process may have different yields, depending on the fragment size and/or sequence. The fragment pooling step may account for the different yields by pooling the fragments at approximately equal concentrations, e.g., by diluting certain fragments or by subjecting lower yield fragments to additional amplification steps. In this manner, the fragment synthesis step may incorporate amplification information as part of the quality feedback. Further, the yield and/or sequencing information from the fragments and/or assembled molecules may be provided as feedback to the design phase. In one embodiment, a particular fragment design set may have poor yield or poor error rates at the fragment and/or assembled molecule level. Such information may be provided back to the design phase and implemented as quality control for future fragment design.

The disclosed techniques may incorporate nucleic acid synthesis (e.g., "writing") in conjunction with sequencing (e.g., "reading") in a single platform (or a plurality of coupled platforms) for ease of analysis. Thus, apparatus and methods for reading and writing nucleic acids are provided herein. Accordingly, the disclosed techniques may be used in conjunction with certain sequencing platforms. In one embodiment, certain sequencing platforms using technologies that may be performed in a template-dependent manner may incorporate an earlier synthesis step to generate the template on the platform in situ. This synthesized template, corresponding to a desired fragment sequence, may then be amplified and sequenced to provide feedback regarding error, quality, design or the like. Accordingly, in contrast to certain PCR or recombinant nucleic acid synthesis techniques, the disclosed techniques may be implemented in an initially template-free manner with a desired synthetic sequence designed in silico.

In one embodiment, a method is provided for synthesizing a nucleic acid. The method can include the steps of (a) providing a plurality of nucleic acid fragments having overlapping sequences, wherein the plurality of nucleic acid fragments have complementary sequences to at least one other fragment of the plurality of nucleic acid fragments, wherein a first fragment of the plurality of nucleic acid fragments has a first cleavable adapter sequence and a 5' end of the target sequence downstream of the first cleavable adapter sequence and wherein a last fragment of the plurality of nucleic acid fragments has a 3' end of the target sequence upstream of a second cleavable adapter sequence; (b) immobilizing the first fragment on a substrate with a first immobilized primer complementary to the first cleavable adapter sequence; (c) assembling the plurality of nucleic acid fragments into an assembled polynucleotide molecule via hybridization of the complementary sequences, wherein the assembled polynucleotide molecule is immobilized on the substrate via the first immobilized primer; (d) amplifying the assembled polynucleotide molecule on the substrate to generate an amplified cluster having amplicons of the assembled polynucleotide molecule on the substrate; and (e) sequencing the amplified cluster.

Also provided is a method for synthesizing nucleic acid fragments that includes steps of (a) providing a plurality of oligonucleotides immobilized on a substrate via hybridization to a plurality of first immobilized primers complementary to the 5' ends of the oligonucleotides, wherein each respective oligonucleotide comprises a first adapter sequence at a 5' end; (b) extending the oligonucleotides to generate extended polynucleotides corresponding to a fragment sequence, wherein the extending includes incorporating a plurality of individual nucleotides or nucleic acids onto a 3' end of the respective oligonucleotides of the plurality of oligonucleotides to generate the extended polynucleotides having the fragment sequence; (c) attaching a second adapter sequence at the 3' ends of the extended polynucleotides having the fragment sequence; (d) annealing the 3' ends of the extended polynucleotides to the substrate via a plurality of second immobilized primers complementary to the 3' ends of the extended polynucleotides to form bridges; (e) amplifying the bridges to form a plurality of amplified clusters; (f) sequencing the plurality of amplified clusters to determine if one or more of the plurality of amplified clusters includes a sequence of the nucleic acid fragment; (g) harvesting the one or more of the plurality of amplified clusters if a sequence of the one or more of the plurality of amplified clusters includes the sequence of the nucleic acid fragment or is complementary to the sequence of the nucleic acid fragment to generated harvested amplified clusters having the fragment sequence; and (h) pooling the harvested amplified clusters having the fragment sequence with a second plurality of amplified clusters, wherein at least a portion of the second plurality of amplified clusters comprises a sequence complementary to only a portion of the fragment sequence.

In some embodiments, a method for synthesizing a nucleic acid can include steps of (a) providing a plurality of target sequences based on a sequence of the nucleic acid, wherein a combination of the plurality of target sequences form the sequence of the nucleic acid; (b) providing a plurality of primer oligonucleotides immobilized on a substrate; (c) extending the primer oligonucleotides in a single-stranded manner based on the plurality of target sequences in the presence of a first polymerase to generate a plurality of fragment polynucleotides; (d) providing a first sequencing reagent to the plurality of fragment polynucleotides in the presence of a second polymerase, wherein the first sequencing reagent has one or more nucleotide monomers, and wherein the one or more nucleotide monomers form a plurality of polynucleotides complementary to at least a portion of the plurality of fragment polynucleotides; (e) providing a second sequencing reagent to the plurality of fragment polynucleotides, wherein the second sequencing reagent includes at least one nucleotide monomer, wherein the at least one nucleotide monomer of the second sequencing reagent includes a reversibly terminating moiety, and wherein the second sequencing reagent is provided subsequent to providing the first sequencing reagent, whereby a sequence of each of the plurality of fragment polynucleotides is obtained; (f) harvesting the plurality of fragment polynucleotides based on comparing the sequence of each of the plurality of fragment polynucleotides with the respective target sequence; and (g) assembling the plurality of fragment polynucleotides to generate an assembled polynucleotide.

This disclosure provides a system for synthesizing a nucleic acid. The system can include (a) a substrate having a plurality of flow channels, each of the plurality of flow channels including a plurality of immobilized primer oligonucleotides; (b) a processor-based device storing executable instructions and coupled to the substrate, wherein the executable instructions are configured to: (i) receive one or more synthesis signals for each respective flow channel indicative of a presence of a first polymerase generating a respective plurality of single-stranded fragment polynucleotides based on one of a plurality of target sequences; (ii) control entry of a first sequencing reagent, a second sequencing reagent, and a second polymerase into the flow channels based on the one or more synthesis signals, wherein the first sequencing reagent includes one or more nucleotide monomers, wherein the one or more nucleotide monomers form a plurality of polynucleotides complementary to at least a portion of the plurality of fragment polynucleotides, wherein the second sequencing reagent includes at least one nucleotide monomer, and wherein the at least one nucleotide monomer of the second sequencing reagent has a reversibly terminating moiety; (iii) receive one or more sequencing signals for each respective flow channel indicative of a presence of the first sequencing reagent and the second sequencing reagent in the presence of the second polymerase; (iv) determine a sequence of each of the plurality of fragment polynucleotides based on the one or more sequencing signals; and (v) provide an indication related to a comparison of the sequence of each of the plurality of fragment polynucleotides with the respective target sequence; and (c) an assembly cell configured to gather each of the plurality of fragment polynucleotides from each of the plurality of flow channels and assemble each of the plurality of fragment polynucleotides to generate an assembled polynucleotide.

Further provides is a method for synthesizing a nucleic acid, including steps of: (a) providing a starting polynucleotide sequence including a target sequence; (b) receiving or accessing information representative of sequences of a plurality of overlapping nucleic acid fragments based on the target sequence, wherein the fragments are designed such that the fragments including the target sequence comprise discontinuities in a 5' to 3' direction, and wherein the discontinuities between nucleic acid fragments occur when the nucleic acid fragments are hybridized on a complementary strand to the target sequence; (c) receiving sequencing information from amplified clusters, wherein the amplified clusters are amplified from bridges generated from synthesized fragments having the sequence of the plurality of nucleic acid fragments; and (d) determining a quality of one or more of the plurality of amplified clusters based on the sequencing information.

DRAWINGS

These and other features, aspects, and advantages of the present invention will become better understood when the following detailed description is read with reference to the accompanying drawings in which like characters represent like parts throughout the drawings.

DETAILED DESCRIPTION

1. Definitions

Figure 1:
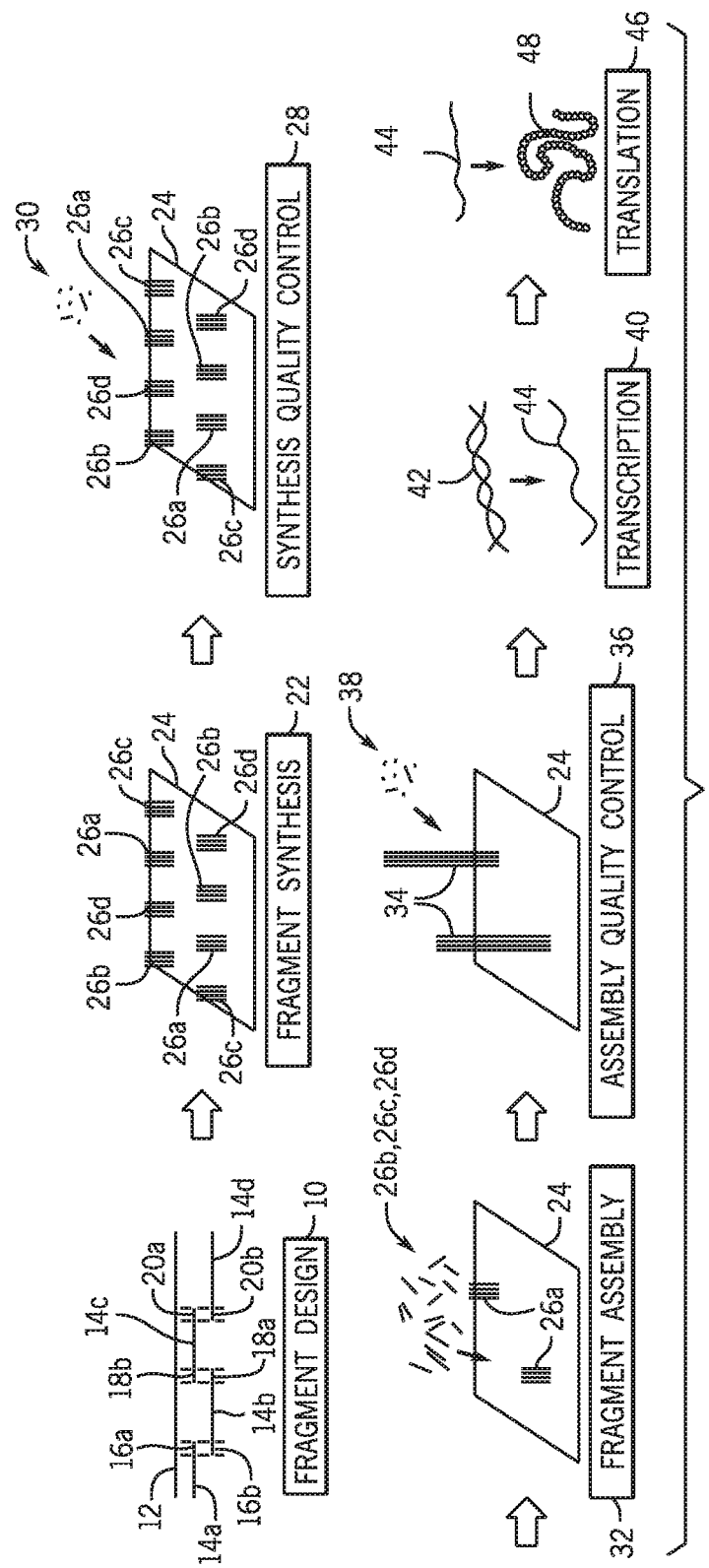
FIG. 1 is a schematic overview of a technique for generating a synthetic polynucleotide molecule, which, in certain embodiments, may be in turn used to create other nucleic acids (e.g., via transcription) and/or proteins (e.g., via translation) according to embodiments of the present disclosure.

As used herein the singular forms "a", "and", and "the" include plural referents unless the context clearly dictates otherwise. Thus, for example, reference to "a cell" includes a plurality of such cells, and so forth. All technical and scientific terms used herein have the same meaning as commonly understood to one of ordinary skill in the art to which this invention belongs unless clearly indicated otherwise.

As used herein, "amplification" and/or grammatical variants thereof refers to any method for increasing the number of copies of a nucleotide sequence using a template nucleic acid having the sequence or its complement. Amplification can be carried out, for example, with a polymerase or ligase. The method can be carried out in vitro, for example in a flow cell or other fluidic vessel. In some embodiments, nucleic acid amplification results in the incorporation of nucleotides into a DNA and/or RNA molecule or primer thereby forming a new molecule complementary to a target nucleic acid. The formed nucleic acid molecule, its complement or both can be used as templates to synthesize additional nucleic acid molecules. As used herein, one amplification reaction may consist of at least one or more rounds of replication. Nucleic acid amplification reactions include, for example, polymerase chain reactions (PCR), random prime amplification, bridge amplification, rolling circle amplification (RCA), ligase chain reaction and other methods known in the art. Examples of useful amplification methods are described in U.S. Patent Application Publication No. 2005/0037393 A1, which is incorporated herein by reference. One PCR reaction may consist of 5 to 100 "cycles" of denaturation and synthesis of a DNA molecule.

Amplification can be carried out in solution or on solid phase. Bridge amplification is a particularly useful method of solid phase amplification. Examples of bridge amplification are described in Bentley et al., Nature 456:53-59 (2008); U.S. Pat. No. 5,641,658 or 7,115,400; or in U.S. Pat. Pub. Nos. 2002/0055100 A1, 2004/0096853 A1, 2004/0002090 A1, 2007/0128624 A1, or 2008/0009420 A1, each of which is incorporated herein by reference in its entirety. Other methods that can be carried out in solution or on solid-phase include, for example, PCR, RCA, MDA and other amplification methods set forth herein or known in the art. Examples of RCA are described in Lizardi et al., Nat. Genet. 19:225-232 (1998) or US Pat. Pub. No. 2007/0099208 A1, each of which is incorporated herein by reference in its entirety. Also useful is multiple displacement amplification (MDA), for example, using a product of RCA (i.e. an RCA amplicon) as a template. Exemplary methods of MDA are described in U.S. Pat. Nos. 6,124,120; 5,871,921; or EP 0,868,530 B1, each of which is incorporated herein by reference in its entirety.

As used herein, "complementary" or "complementarity" and/or grammatical variants thereof refers to the degree of base-pairing or hybridization between nucleic acids. For example, as is known to those skilled in the art, adenine (A) can form hydrogen bonds or base pair with thymine (T) or uracil (U) and guanine (G) can form hydrogen bonds or base pair with cytosine (C). Hence, A is complementary to T or U and G is complementary to C. These are the standard "Watson-Crick" base pairs occurring in the vast majority of DNA and RNA hybrids in vivo. Complementarity, when used in reference to a double stranded region of nucleic acid may be complete when all bases in the double-stranded region are base paired. Alternatively, complementarity may be "partial," in which only some of the bases in the double stranded region are matched according to the base pairing rules. The degree of complementarity between nucleic acid strands has an effect on the efficiency and strength of hybridization between nucleic acid strands. "Complementary" sequences can also include, or be formed entirely from, non-Watson-Crick base pairs and/or base pairs formed from non-natural and modified nucleotides, in so far as the above requirements with respect to their ability to hybridize are fulfilled.

As used herein, "error rate" and/or grammatical variants thereof refers to the relative number of erroneous nucleotides in a polynucleotide sequence, as compared to the number of the nucleotides in a target polynucleotide sequence. The erroneous nucleotide refers to the nucleotide in the polynucleotide sequence that is different from the corresponding nucleotide in the target polynucleotide sequence when the polynucleotide sequence and the target polynucleotide sequence are aligned. The error rate can be presented in a variety of formats including, but not limited to, a ratio or fraction of the number of erroneous nucleotides in a sequence to the number of total nucleotides in a particular sequence. For example, when a target polynucleotide has a sequence of AAAAA, and a synthesized polynucleotide based on the target polynucleotide has a sequence of AAAAG, the error rate is ⅕, or 20%.

As used herein, "hybridization" and/or grammatical variants thereof refers to the physical interaction of complementary (including partially complementary) polynucleotide strands by the formation of hydrogen bonds between complementary nucleotides when the strands are arranged antiparallel to each other. Hybridization and the strength of hybridization (e.g., the strength of the association between polynucleotides) is impacted by many factors well known in the art including the degree of complementarity between the polynucleotides, and the stringency of the conditions involved, which is affected by such conditions as the concentration of salts, the presence of other components (e.g., the presence or absence of polyethylene glycol), the molarity of the hybridizing strands and the G+C content of the polynucleotide strands, all of which results in a characteristic melting temperature (Tm) of the formed hybrid. The terms "hybridization (hybridize)" and "binding," when used in reference to nucleic acids, can be used interchangeably and can refer to the process by which single strands of nucleic acid sequences form double-helical segments through hydrogen bonding between complementary nucleotides. "Hybrid," "duplex," and "complex," when used in reference to nucleic acids, can also be used interchangeably herein referring to a double-stranded nucleic acid molecule formed by hybridization (e.g., DNA-DNA, DNA-RNA, and RNA-RNA species).

As used herein, "nucleic acid" and/or grammatical variants thereof includes polymers of deoxyribonucleotides or ribonucleotides in either single- or double-stranded form. The term can include such polymers that are composed of monomers (nucleotides) containing a sugar, phosphate and a base that is either a purine or pyrimidine. Unless specifically limited, the term encompasses nucleic acids containing analogs of natural nucleotides that have similar binding properties as the reference nucleic acid and/or nucleic acids having non-native backbones such as protein nucleic acids. In particular embodiments, nucleotide analogs are also metabolized in a manner similar to naturally occurring nucleotides. Reference to a particular nucleic acid sequence can implicitly refer to its complementary sequences as well as the reference sequence explicitly indicated. For example, teaching related to amplifying a nucleic acid sequence will be understood to include embodiments where one or more copies of the sequence, its complement or both are produced, unless explicitly stated to the contrary.

As used herein, "nucleotide" and/or grammatical variants thereof refers to a base-sugar-phosphate combination. Nucleotides are monomeric units of a nucleic acid sequence (DNA and RNA). The term nucleotide includes ribonucleoside triphosphate ATP, UTP, CTP, GTP and deoxyribonucleoside triphosphates such as dATP, dCTP, dITP, dUTP, dGTP, dTTP, or derivatives thereof "Nucleotide" as used herein also refers to dideoxyribonucleoside triphosphates (ddNTPs) and their derivatives including, but not limited to, ddATP, ddCTP, ddGTP, ddITP, and ddTTP. In one embodiment of the present disclosure, a "nucleotide" may be unlabeled or detectably labeled by well known techniques. Detectable labels include, but are not limited to, radioactive isotopes, fluorescent labels, chemiluminescent labels, bioluminescent labels, and enzyme labels.

As used herein, "nucleic acid fragment" and/or grammatical variants thereof refers to a synthetic or natural molecule comprising a covalently linked sequence of nucleotides that is shorter than a reference nucleic acid. The nucleotides can be joined by a phosphodiester bond between the 3' position of the deoxyribose or ribose of one nucleotide and the 5' position of the deoxyribose or ribose of the adjacent nucleotide. A nucleic acid fragments can include natural (e.g., A, G, C, T or U) or modified bases (e.g., 7-deazaguanosine, inosine). In addition, the bases in a nucleic acid fragments can be joined by a linkage other than a phosphodiester bond, so long as it does not interfere with hybridization of the nucleic acid fragment. Thus, nucleic acid fragments can be peptide nucleic acids in which one or more of the constituent bases are joined by peptide bonds rather than phosphodiester linkages. Nucleic acid fragments may be single-stranded or double-stranded. Although a nucleic acid fragment can be created from a longer reference nucleic acid, it will be understood that the term "fragment" is intended to refer to the comparative lengths of two nucleic acids and not necessarily the origins or method of creating either of the two nucleic acids. Typically a nucleic acid fragment will have a sequence that is identical or perfectly complementary to a portion of a reference nucleic acid. However, in some embodiments the fragment may be less than perfectly homologous or complementary to the portion of the reference sequence, for example, being at least 80%, 85%, 90%, 95%, 99% or 99.9% homologous or complementary to the portion of the reference sequence.

As used herein, "primer" and/or grammatical variants thereof refers to a single-stranded oligonucleotide that is extended by covalent bonding of nucleotide monomers during amplification or polymerization of a nucleic acid molecule. A primer can be naturally occurring as in a purified restriction digest or produced synthetically. A primer is typically capable of acting as a point of initiation of sample-dependent nucleic acid synthesis. The primer may be either single-stranded or double-stranded and, in particular embodiments, must be sufficiently long to prime the synthesis of the desired extension product in the presence of the chosen polymerase. The exact length of the primer will depend upon many factors, including hybridization and polymerization temperatures, source of primer and the method used. For example, a primer can comprise about at least 15-75 nucleotides, although it may contain fewer or more nucleotides. The factors involved in determining the appropriate length of primer for a particular application will readily known or determinable to one of ordinary skill in the art based on the teaching set forth herein.

The term 'immobilized' as used herein is intended to encompass direct or indirect attachment to a solid support via covalent or non-covalent bond(s). In certain embodiments, covalent attachment may be used, but generally all that is required is that the molecules (for example, nucleic acids) remain bound or attached to a support under conditions in which it is intended to use the support, for example in applications requiring nucleic acid amplification and/or sequencing. Typically oligonucleotides to be used as capture oligonucleotides or amplification oligonucleotides are immobilized such that a 3' end is available for enzymatic extension and at least a portion of the sequence is capable of hybridizing to a complementary sequence. Immobilization can occur via hybridization to a surface attached oligonucleotide, in which case the immobilized oligonucleotide or polynucleotide may be in the 3'-5' orientation. Alternatively, immobilization can occur by means other than base-pairing hybridization, such as the covalent attachment set forth above. In some embodiments, nucleic acid molecules can be attached to a solid support or other surface via a gel layer as described, for example, in U.S. patent application Ser. No.

13/784,368 and US Pat. App. Pub. No. 2011/0059865 A1, each of which is incorporated herein by reference.

As used herein "solid support," "solid-phase," "support," and "substrate" and/or grammatical variants thereof refers to any material that provides a substantially rigid structure or structure that retains its shape rather than taking on the shape of a vessel to which it is placed. The material can have a surface to which another material can be attached including but not limited to smooth supports (e.g., metal, glass, plastic, silicon, and ceramic surfaces) as well as textured and porous materials. Substrate materials include, but are not limited to acrylics, carbon (e.g., graphite, carbon-fiber), cellulose (e.g., cellulose acetate), ceramics, controlled-pore glass, cross-linked polysaccharides (e.g., agarose or SEPHAROSE®), gels, glass (e.g., modified or functionalized glass), gold (e.g., atomically smooth Au(111)), graphite, inorganic glasses, inorganic polymers, latex, metal oxides (e.g., $SiO_2$, $TiO_2$, stainless steel), metalloids, metals (e.g., atomically smooth Au(111)), mica, molybdenum sulfides, nanomaterials (e.g., highly oriented pyrolitic graphite (HOPG) nanosheets), nitrocellulose, NYLON®, optical fiber bundles, organic polymers, paper, plastics, polacryloylmorpholide, poly(4-methylbutene), poly(ethylene terephthalate), poly(vinyl butyrate), polybutylene, polydimethylsiloxane (PDMS), polyethylene, polyformaldehyde, polymethacrylate, polypropylene, polysaccharides, polystyrene, polyurethanes, polyvinylidene difluoride (PVDF), quartz, rayon, resins, rubbers, semiconductor material, silica, silicon (e.g., surface-oxidized silicon), sulfide, and TEFLON®.

Substrates can have a flat surface but need not be flat and can include any type of shape including spherical shapes (e.g., beads), porous shapes (e.g. gels) or cylindrical shapes (e.g., fibers). Materials attached to solid supports may be attached to any portion of the solid support (e.g., may be attached to an interior portion of a porous solid support material).

Substrates may be patterned, where a pattern (e.g., spots, pads, wells, posts, stripes, swirls, lines, triangles, rectangles, circles, arcs, checks, plaids, diagonals, arrows, squares, or cross-hatches) is etched, printed, treated, sketched, cut, carved, engraved, imprinted, fixed, stamped, coated, embossed, embedded, or layered onto a substrate. The pattern can comprise one or more cleavage regions or modified regions on the substrate.

A biological material is "attached" to a substrate when it is associated with or bound to the solid substrate through a stable chemical or physical interaction. In some preferred embodiments, the attachment is through a covalent bond. However, attachments need not be covalent or permanent. In one embodiment, materials are attached to a substrate through a "spacer molecule" or "linker group." Such spacer molecules are molecules that have a first portion that attaches to the biological material and a second portion that attaches to the substrate. Thus, when attached to the substrate, the spacer molecule intervenes the substrate and the biological materials, but is attached to both. Methods of attaching biological material (e.g., nucleic acid, affinity ligand receptor, enzyme, chemical hydroxyl radical generator) to a substrate are well known in the art, and include but are not limited to chemical coupling.

As used herein, "sequencing reagent" and grammatical equivalents thereof refers to a composition, such as a solution, comprising one or more reactant, catalyst or label or other analyte that participates in a reaction to determine the order of monomers (e.g. nucleotides) in a polymer (e.g. nucleic acid). In some embodiments, such as a sequencing-by-synthesis embodiment, a sequencing reagent includes one or more nucleotide monomers having a label moiety, a terminator moiety, or both. Such moieties are chemical groups that are often not naturally occurring moieties of nucleic acids, being introduced by synthetic means to alter the natural characteristics of the nucleotide monomers with regard to detectability under particular conditions or enzymatic reactivity under particular conditions. Alternatively, a sequencing reagent comprises one or more nucleotide monomers that lack a non-natural label moiety and/or a non-natural terminator moiety. In some embodiments, the sequencing reagent consists of or consists no more than one nucleotide monomer type, two different nucleotide monomer types, three different nucleotide monomer types or four different nucleotide monomer types. "Different" nucleotide monomer types are nucleotide monomers that have base moieties that are not the same as each other. Two or more nucleotide monomer types can have other moieties, such as those set forth above, that are the same as each other or different from each other.

For ease of illustration, various methods and compositions are described herein with respect to multiple nucleotide monomers. It will be understood that the multiple nucleotide monomers of these methods or compositions can be of the same or different types unless explicitly indicated otherwise. It should be understood that when providing a sequencing reagent comprising multiple nucleotide monomers to a target nucleic acid, the nucleotide monomers do not necessarily have to be provided at the same time. However, in preferred embodiments of the methods described herein, multiple nucleotide monomers are provided together (at the same time) to the target nucleic acid. Irrespective of whether the multiple nucleotide monomers are provided to the target nucleic acid separately or together, the result can be that the sequencing reagent, including the nucleotide monomers contained therein, are simultaneously in the presence of the target nucleic acid. For example, two nucleotide monomers can be delivered, either together or separately, to a target nucleic acid. In such embodiments, a sequencing reagent comprising two nucleotide monomers will have been provided to the target nucleic acid. Alternatively, different nucleotide types can be delivered sequentially in a cycle that includes delivery and removal of each nucleotide type such that the different nucleotide types are not simultaneously present with the target nucleic acid. In some embodiments, zero, one or two of the nucleotide monomers will be incorporated into a polynucleotide that is complementary to the target nucleic acid. In some embodiments, a sequencing reagent may comprise an oligonucleotide that may be incorporated into a polymer. The oligonucleotide may comprise a terminator moiety and/or a label moiety.

As used herein, "a sequencing run" and/or grammatical variants thereof refers to a repetitive process of physical or chemical steps that is carried out to obtain signals indicative of the order of monomers in a polymer. The signals can be indicative of an order of monomers at single monomer resolution or lower resolution. In particular embodiments, the steps can be initiated on a nucleic acid target and carried out to obtain signals indicative of the order of bases in the nucleic acid target. The process can be carried out to its typical completion, which is usually defined by the point at which signals from the process can no longer distinguish bases of the target with a reasonable level of certainty. If desired, completion can occur earlier, for example, once a desired amount of sequence information has been obtained. In some embodiments, a sequencing run is composed of several cycles, where each cycle includes a series of two or more steps, and the series of steps is repeated in each cycle.

For example, a 10 cycles of a sequencing-by-synthesis run can be carried out to identify a sequence of 10 nucleotides. Each of the 10 cycles can include steps of polymerase catalyzed extension of a primer to add a nucleotide analog having a blocking moiety and label moiety; detecting the label moiety on the extended primer; and removing the label moiety and blocking moiety from the extended primer.

A sequencing run can be carried out on a single target nucleic acid molecule or simultaneously on a population of target nucleic acid molecules having the same sequence, or simultaneously on a population of target nucleic acids having different sequences. In some embodiments, a sequencing run is terminated when signals are no longer obtained from one or more target nucleic acid molecules from which signal acquisition was initiated. For example, a sequencing run can be initiated for one or more target nucleic acid molecules that are present on a solid phase substrate and terminated upon removal of the one or more target nucleic acid molecules from the substrate. Sequencing can be terminated by otherwise ceasing detection of the target nucleic acids that were present on the substrate when the sequencing run was initiated. Sequencing can be carried out using any suitable sequencing technique, such as those described in U.S. Patent Application Publication No. 2012/0122737 A1, which is incorporated herein by reference.

As used herein, the term "surface" and/or grammatical variants thereof refers to a part of a support structure (e.g., substrate) that is accessible to contact with reagents, beads or analytes. The surface can be substantially flat or planar. Alternatively, the surface can be rounded or contoured. Exemplary contours that can be included on a surface are wells, depressions, pillars, ridges, channels or the like. Exemplary materials that can be used as a support structure include, but are not limited to acrylics, carbon (e.g., graphite, carbon-fiber), cellulose (e.g., cellulose acetate), ceramics, controlled-pore glass, cross-linked polysaccharides (e.g., agarose or SEPHAROSE®), gels, glass (e.g., modified or functionalized glass), gold (e.g., atomically smooth Au(111)), graphite, inorganic glasses, inorganic polymers, latex, metal oxides (e.g., SiO2, TiO2, stainless steel), metalloids, metals (e.g., atomically smooth Au(111)), mica, molybdenum sulfides, nanomaterials (e.g., highly oriented pyrolitic graphite (HOPG) nanosheets), nitrocellulose, NYLON®, optical fiber bundles, organic polymers, paper, plastics, polacryloylmorpholide, poly(4-methylbutene), polyethylene terephthalate), poly(vinyl butyrate), polybutylene, polydimethylsiloxane (PDMS), polyethylene, polyformaldehyde, polymethacrylate, polypropylene, polysaccharides, polystyrene, polyurethanes, polyvinylidene difluoride (PVDF), quartz, rayon, resins, rubbers, semiconductor material, silica, silicon (e.g., surface-oxidized silicon), sulfide, and TEFLON®. A single material or mixture of several different materials can form a surface useful in the embodiments herein. The terms "surface" and "substrate" are used interchangeably herein.

2. General Techniques(s) of the Present Disclosure

The present disclosure provides improved techniques for nucleic acid synthesis. The techniques may incorporate nucleic acid sequencing into one or more quality control steps of the synthesis. The sequencing may facilitate harvesting error-free synthetic nucleic acids selected or harvested from a field of synthetic molecules. In addition, the techniques may allow synthesis and sequencing (writing and reading) to occur on a single apparatus so that the error rate of the synthesis may be controlled and quantified for individual synthetic molecules. In some cases, writing and reading can occur simultaneously or in rapid succession. As such, the present disclosure describes systems and methods for developing a synthesis and sequencing device (write and read device) to bring synthetic biology to routine biological work.

Furthermore, the techniques set forth herein may be performed in a template-independent manner. More specifically, a nucleic acid can be synthesized de novo, for example, by assembling nucleic acid fragments absent interactions of the fragments with a template nucleic acid. The fragments themselves can be synthesized without use of a template, for example, using a chemical synthesis technique or using a template independent enzyme. It will nonetheless be understood that template-dependent synthesis methods can be used to generate fragments or to assemble fragments as desired to suit some embodiments.

Turning now to the drawings, and referring first to FIG. 1, a schematic overview of a technique is illustrated for generating a synthetic polynucleotide molecule, which, in certain embodiments, may be in turn used to create other nucleic acids (e.g., via transcription) and/or proteins (e.g., via translation) according to embodiments of the present disclosure. The nucleic acid synthesis may start with a fragment design phase 10. The fragment design phase 10 may include using information about a target nucleic acid sequence 12 to design sequences for one or more nucleic acid fragments (e.g., fragments 14a, 14b, 14c, 14d). Although four nucleic acid fragments (e.g., fragments 14a, 14b, 14c, 14d) are illustrated in FIG. 1, it is understood that sequences for any number (e.g., at least 1, 2, 3, 4, 5, 6, 7, 8, 9, 10, or more) of nucleic acid fragments may be designed based on the target nucleic acid sequence 12.

As illustrated, each of the nucleic acid fragments 14a, 14b, 14c, 14d includes a complementary sequence to at least one other nucleic acid fragments 14a, 14b, 14c, 14d. For example, the nucleic acid fragment 14a has a complementary sequence (e.g., a sequence 16a) to a sequence (e.g., a sequence 16b) of the nucleic acid fragment 14b, illustrated by an overlapping region. The nucleic acid fragment 14b has a complementary sequence (e.g., a sequence 18a) to a sequence (e.g., a sequence 18b) of the nucleic acid fragment 14c. The nucleic acid fragment 14c has a complementary sequence (e.g., a sequence 20a) to a sequence (e.g., a sequence 20b) of the nucleic acid fragment 14d. In certain embodiments, the complementary sequence is complementary to only a portion of another fragment. That is, the complementary sequence 16a represents only a portion of the fragment 14a. Further, the complementary sequences 16b and 18b represent only a portion of the fragment 14b. In particular embodiments the complementary sequence portions are found at the ends of the fragments.

In some embodiments, the sequences of nucleic acid fragments 14a, 14b, 14c, 14d may be designed based on the target nucleic acid sequence 12 such that the nucleic acid fragment sequences 14a, 14b, 14c, 14d have a combined sequence (with the overlapping sequences counted once) that is the same as or complementary to the target nucleic acid sequence 12. For example, the overall sequence, including the sequence of the nucleic acid fragment 14a, the sequence of the nucleic acid fragment 14b without the sequences 16b, 18a, the sequence of the nucleic acid fragment 14c, and the sequence of the nucleic acid fragment 14d without the sequence 20b, is the same as or complementary to the target nucleic acid sequence 12. In this embodiment, there are no gaps in the combined sequence of the fragments compared to the target nucleic acid sequence. As set forth in detail below, in alternative embodiments, gaps may be present in the combined sequence of the nucleic acid fragments (e.g. between the sequences of the fragments) compared to the target nucleic acid sequence.

The target nucleic acid sequence 12 generally has at least two nucleotides. For example, the target nucleic acid sequence 12 may be at least about 10, 25, 50, 100, 150, 200, 250, 300, 350, 400, 450, 500, 550, 600, 650, 700, 750, 800, 850, 900, 950 bases, as well as about 1, 2, 3, 4, 5, 6, 7, 8, 9, or 10 kb, as well as about 11, 12, 13, 14, 15, 16, 17, 18, 19, or 20 kb, as well as about 25, 30, 35, 40, 45, 50, 55, 60, 65, 70, 75, 80, 85, 90, 95 or 100 kb, as well as about 200, 300, 400, 500, 600, 700, 800, 900, or 1,000 kb and all increments therein. Alternatively or additionally, the target nucleic acid sequence 12 may be no more than about 100, 150, 200, 250, 300, 350, 400, 450, 500, 550, 600, 650, 700, 750, 800, 850, 900, 950 bases, as well as about 1, 2, 3, 4, 5, 6, 7, 8, 9, or 10 kb, as well as about 11, 12, 13, 14, 15, 16, 17, 18, 19, or 20 kb, as well as about 25, 30, 35, 40, 45, 50, 55, 60, 65, 70, 75, 80, 85, 90, 95 or 100 kb, as well as about 200, 300, 400, 500, 600, 700, 800, 900, or 1,000 kb.

The sequences of the nucleic acid fragments 14a, 14b, 14c, 14d generally have at least two nucleotides. For example, the nucleic acid fragments 14a, 14b, 14c, 14d may be at least about 10, 25, 50, 100, 150, 200, 250, 300, 350, 400, 450, 500, 550, 600, 650, 700, 750, 800, 850, 900, 950 bases, and all increments therein. Alternatively or additionally, the nucleic acid fragments 14a, 14b, 14c, 14d may be at no more than about 10, 25, 50, 100, 150, 200, 250, 300, 350, 400, 450, 500, 550, 600, 650, 700, 750, 800, 850, 900, or 950 bases.

The overlapping complementary sequences of the nucleic acid fragments 14a, 14b, 14c, 14d (e.g., sequences 16a, 16b, 18a, 18b, 20a, 20b) generally have at least one nucleotide. For example, the overlapping sequences of the nucleic acid fragments 14a, 14b, 14c, 14d may be more or less than 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950 bases and all increments therein. In particular embodiments, the overlapping sequences of the nucleic acid fragments 14a, 14b, 14c, 14d may be between 1 and 50 bases in length, such as between 5 and 45 bases, between 10 and 40 bases, between 15 and 35 bases, between 20 and 30 bases. In particular embodiments, the overlapping or complementary sequences may be shorter than the size of the fragments 14 they are a part of. For fragments with two complementary overlaps, the complementary sequences are each less than half of the total fragment size.

The fragment design phase 10 is then followed by a fragment synthesis phase 22. In one embodiment, one or more nucleic acid fragments 14a, 14b, 14c, 14d are synthesized on a substrate 24. The synthesis of the nucleic acid fragments 14a, 14b, 14c, 14d may be carried out by extension of immobilized primers on the substrate 24 with successively adding nucleotides to a free 3' hydroxyl group, resulting in synthesis in the 5' to 3' direction of polynucleotides targeting the nucleic acid fragments 14a, 14b, 14c, 14d. In a specific embodiment, the fragment synthesis may be carried out in the presence of a polymerase, such as terminal deoxynucleotidyl transferase (TdT).

The synthesis exemplified in FIG. 1, can be performed in the absence of a template since TdT can add nucleotides without a template. In particular embodiments, a primer that is immobilized on substrate 24 is sequentially treated with different types of nucleotide analogs in the presence of TdT. The nucleotide types will differ with respect to which base is present on the nucleotide. The order of nucleotide analog types delivered to the primer will determine the sequence of the fragment produced. Furthermore, the nucleotide analogs can include a reversible blocking moiety to prevent addition of more than one nucleotide to the primer per cycle. In this case a cycle can include (1) delivery of the appropriate type of reversibly blocked nucleotide analog to the surface-immobilized primer, in the presence of TdT, whereby a single nucleotide analog is added to the 3' end of the primer to create an extended primer; (2) washing away unreacted nucleotide analog (and optionally TdT) from the substrate 24; and (3) removal of the blocking moiety from the nucleotide analog at the 3' end of the extended primer. Particular embodiments can use a species TdT, or engineered variant of a TdT species that has desired activity for nucleotides having a particular blocking group. Such TdT species can be created using known mutagenesis techniques and screening for polymerase activity using the particular nucleotide species in known polymerase assays.

Alternatively, the synthesis of the nucleic acid fragments 14a, 14b, 14c, 14d may be carried out by extension of immobilized primers on the substrate 24 by successively adding nucleotides in the 3' to 5' direction. For example, chemical synthesis can be carried out in a well known cyclical process that assembles a chain of nucleotides. Nucleotides are added one by one through a cycle of chemical reactions, in which a particular molecule (e.g., a nucleotide) is added to a growing DNA molecule (e.g., a growing DNA chain), sometimes via catalysis, until the desired chain is complete. Generally, each cycle of chemical reactions includes the steps of detritylation, coupling, capping and oxidation. During the detritylation or "deprotection" step, a dimethoxytrityl (DMT) group is removed from the last nucleotide of the growing DNA chain to allow the addition of the next nucleotide. The amount of DMT released from each cycle can be monitored to determine coupling efficiency. The release of DMT is apparent because a bright orange color is emitted as DMT is released. Exemplary chemical synthesis methods that can be used are set forth in U.S. Pat. No. 7,914,739 or US Pat. App. Pub. No. 2004/0219063 A1, each of which is incorporated herein by reference in its entirety for all purposes.

Another useful synthetic method is to create a nucleic acid fragment by sequentially adding trinucleotides (i.e. oligonucleotide 3mers). In a particular embodiment, 64 trinucleotides can be synthesized, for example, using a chemical synthesis method such as those set forth above. In this example the 64 trinucleotides correspond to the codons for the 20 naturally occurring amino acids. The trinucleotides can be ligated together using circligase (Epicentre, WI). Ligation can be carried out in a 5' to 3' direction or alternatively in a 3' to 5' direction. Either way, the resulting fragment will code for a number of amino acids that correspond to the number of trinucleotides that were ligated together. And the sequence of the amino acids will correspond to the sequence of trinucleotide addition used for synthesizing the nucleic acid fragment.

In particular embodiments of ligation-based synthesis, it is useful to use trincletoides that have a reversible blocking moiety at the 5' or 3' end. For example, when synthesizing a nucleic acid fragment in the 5' to 3' direction, it is helpful to use trinucleotides that are blocked at the 3' position. In this case, each cycle of addition can be carried out by delivering a solution of trinucleotides for a first codon to a nascent fragment in the presence of circligase. The fragment can be attached via the 5' end to a solid support, or the 5' end can be otherwise blocked to prevent ligation. As a result, the desired ligation event will result in ligation between the 3' end of the nascent fragment and the 5' end of the incoming trinucleotide. Addition of more than one trinucleotide per cycle is prevented because, once extended by addition of a single trunucleotide, the nascent fragment will now have a 3' blocking group that prevents further extension. Excess trinucleotides can be removed, for example by washing, and then the 3' blocking group can be removed or modified to generate an unblocked 3' end on the extended nascent fragment. A second cycle can then be carried out by delivering a solution of trinucleotides for a second codon to the nascent fragment that was previously extended and deblocked, again, in the presence of circligase.

Trinucleotide ligation can also be carried out in the 3' to 5' direction. The trinucleotides can optionally be blocked at the 5' position and the nascent fragment can optionally be blocked or attached to a surface via the 3' end. Each cycle of addition can be carried out by delivering a solution of trinucleotides for a first codon to a nascent fragment in the presence of circligase, thereby extending the nascent fragment due to ligation between the 5' end of the nascent fragment and the 3' end of the incoming trinucleotide. Excess trinucleotides can be removed, for example by washing, and then the 5' blocking group can be removed or modified to generate an unblocked 5' end on the extended nascent fragment. A second cycle can then be carried out by delivering a solution of trinucleotides for a second codon to the nascent fragment that was previously extended and deblocked, in the presence of circligase. It will be understood that although exemplified for trinucleotides, a similar ligation synthesis can be carried out using 4mer oligonucleotides, 5mer oligonucleotides, timer oligonucleotides, or larger oligonucleotides for ligation to a nascent fragment.

As illustrated, polynucleotides 26a, 26b, 26c, 26d, targeting the sequences of the nucleic acid fragments 14a, 14b, 14c, 14d, respectively, may be synthesized on the substrate 24. In addition, an amplification of synthesized polynucleotides 26a, 26b, 26c, 26d may be performed on the substrate 24 to generate clusters of polynucleotides 26a, 26b, 26c, 26d. The amplification on the substrate 24 may be carried out using bridge amplification, solid-phase PCR, rolling circle amplification (RCA), or any other suitable methods as noted above. In some embodiments, the amplification of the synthesized polynucleotides 26a, 26b, 26c, 26d is optional.

The fragment synthesis phase 22 may be followed by a synthesis quality control phase 28 in which the synthesized polynucleotides 26a, 26b, 26c, 26d are sequenced and the sequences of the synthesized polynucleotides 26a, 26b, 26c, 26d are compared with the sequences of their respective nucleic acid fragments 14a, 14b, 14c, 14d. A sequencing run may be carried out successively or in parallel for the synthesized polynucleotides 26a, 26b, 26c, 26d or their amplification clusters. The sequencing run may be carried out as described in the U.S. Patent Application Publication No. 2010/0279882 A1, or U.S. Pat. No. 8,637,242, which are incorporated herein by reference. As illustrated, the sequencing run may include utilizing a sequencing reagent 30 including one or more nucleotides having a label moiety, a terminator moiety, or both.

After the sequencing run is carried out, a sequence of each of the synthesized polynucleotides 26a, 26b, 26c, 26d or their amplification clusters may be obtained. By then comparing the sequence of each of the synthesized polynucleotides 26a, 26b, 26c, 26d, and/or its complementary sequence in the case of amplification clusters, with the sequence of their respective nucleic acid fragments 14a, 14b, 14c, 14d, a synthesis error rate may be determined. In some embodiments, a corresponding sequence accuracy score (e.g., by subtracting the error rate from one) may also be determined for each of the synthesized polynucleotides 26a, 26b, 26c, 26d or their amplification clusters. Generally, substrate 24 will include a redundancy of sites for each desired fragment. For example, each fragment may be redundantly synthesized at least 2, 4, 5, 10, 25, 50, 100 or more sites on a substrate. The number of redundant sites can be determined to produce a desired number of accurate sites based on the expected error rate for the synthesis procedure being used. Thus, although some sites may contain fragments with errors in their sequences, other sites with accurate sequences can be identified and the fragments harvested from those sites as set forth in further detail below.

By incorporating sequencing into the synthesis quality control phase 28, the sequencing data may be used for nucleic acid synthesis quality control. For example, a synthesis error rate that is determined by the sequencing may be used to determine how well the fragment design was. By way of further example, a lower synthesis error rate of each of the synthesized polynucleotides 26a, 26b, 26c, 26d or their amplification clusters may represent a better fragment design of their respective nucleic acid fragments 14a, 14b, 14c, 14d. Conversely, a higher synthesis error rate of each of the synthesized polynucleotides 26a, 26b, 26c, 26d or their amplification clusters may represent a poorer fragment design of their respective nucleic acid fragments 14a, 14b, 14c, 14d. As such, a predetermined threshold of synthesis error rate may be set and used to compare with the synthesis error rate of each of the synthesized polynucleotides 26a, 26b, 26c, 26d or their amplification clusters determined by the sequencing to determine whether their respective designed fragments are desirable. For example, the predetermined threshold error rate may be at most about 0.00%, 0.01%, 0.02%, 0.03%, 0.04%, 0.05%, 0.06%, 0.07%, 0.08%, 0.09%, 0.10%, 0.15%, 0.20%, 0.25%, 0.30%, 0.35%, 0.40%, 0.45%, 0.50%, 0.55%, 0.60%, 0.65%, 0.70%, 0.75%, 0.80%, 0.85%, 0.90%, 0.95%, 1.00%, 1.10%, 1.20%, 1.30%, 1.40%, 1.50%, 1.60%, 1.70%, 1.80%, 1.90%, 2.00%, 2.10%, 2.20%, 2.30%, 2.40%, 2.50%, 2.60%, 2.70%, 2.80%, 2.90%, 3.00%, 4.00%, 5.00%, 6.00%, 7.00%, 8.00%, 9.00%, 10.00%, 15.00%, 20.00%, 25.00%, 30.00%, 35.00%, 40.00%, 45.00%, 50.00%, 55.00%, 60.00%, 65.00%, 70.00%, 75.00%, 80.00%, 85.00%, 90.00%, 95.00%, 100%. This information can be used to design a different set of fragment sequences. The synthesis and QC procedure can be repeated several times to allow iterative improvement in sequence quality.

In addition, the synthesis error rate determined by the sequencing in the synthesis quality control phase 28 may be used to determine how to harvest the synthesized polynucleotides 26a, 26b, 26c, 26d or their amplification clusters. For example, the synthesized polynucleotides 26a, 26b, 26c, 26d or their amplification clusters may be selectively harvested when their respective error rate is equal to, less than, or higher than a predetermined threshold error rate. The predetermined threshold error rate may be at most about 0.00%, 0.01%, 0.02%, 0.03%, 0.04%, 0.05%, 0.06%, 0.07%, 0.08%, 0.09%, 0.10%, 0.15%, 0.20%, 0.25%, 0.30%, 0.35%, 0.40%, 0.45%, 0.50%, 0.55%, 0.60%, 0.65%, 0.70%, 0.75%, 0.80%, 0.85%, 0.90%, 0.95%, 1.00%, 1.10%, 1.20%, 1.30%, 1.40%, 1.50%, 1.60%, 1.70%, 1.80%, 1.90%, 2.00%, 2.10%, 2.20%, 2.30%, 2.40%, 2.50%, 2.60%, 2.70%, 2.80%, 2.90%, 3.00%, 4.00%, 5.00%, 6.00%, 7.00%, 8.00%, 9.00%, 10.00%, 15.00%, 20.00%, 25.00%, 30.00%, 35.00%, 40.00%, 45.00%, 50.00%, 55.00%, 60.00%, 65.00%, 70.00%, 75.00%, 80.00%, 85.00%, 90.00%, 95.00%, 100%. In some embodiments, the error rates of the synthesized polynucleotides 26a, 26b, 26c, 26d or their amplification clusters may be compared, and those synthesized polynucleotides that have the lowest, the highest, or equal to, less than, or higher than a predetermined threshold error rate may be selectively harvested.

As the sequence of each of the synthesized polynucleotides 26a, 26b, 26c, 26d or their amplification clusters may be obtained by sequencing, a yield of a predetermined synthesized sequence of one of the nucleic acid fragments 14a, 14b, 14c, 14d may also be determined. For example, a predetermined synthesized sequence of the nucleic acid fragment 14a may be an error free sequence (e.g., with a synthesis error rate is about 0.0%), and if the sequence of all of the synthesized polynucleotides 26a (e.g., a single copy or multiple copies in the amplification cluster) are determined to be the error free sequence, then the yield of an error free sequence of the nucleic acid fragment 14a from synthesis is 100%. In some embodiments, a yield of synthesized sequences with a predetermined error rate, regardless of the actual sequences, of one of the nucleic acid fragments 14a, 14b, 14c, 14d may be determined from sequencing. For example, in all 100 of the synthesized polynucleotides 26a in the amplification cluster that are sequenced, there are 90 polynucleotides 26a (e.g., with or without the same sequence) that have a synthesis error rate of about 0.05%. Thus, the yield of the synthesized polynucleotides 26a that have a synthesis error rate of about 0.05% is 90%.

As such, in addition to the synthesis error rate, or alternatively, the yield of a predetermined synthesized sequence and/or synthesized sequences with a predetermined error rate may be used for nucleic acid synthesis quality control in the synthesis quality control phase 28. Similar to the synthesis error rate, such yield may be used to determine how well the fragment design was and/or to determine how to harvest the synthesized polynucleotides 26a, 26b, 26c, 26d or their amplification clusters.

As set forth above, fragments can be amplified on a surface prior to sequencing. Amplification can be carried out to create a colony (also referred to as a "cluster") of copies to form a feature on the surface. Multiple fragments can be synthesized and amplified on a surface to create an array of features. It is possible that the amplification process can introduce errors to produce a mixed cluster containing some copies of the originally synthesized fragment and other copies containing the error. The presence of an amplification error at a cluster or feature can be recognized by the presence of a mixed signal at one or more nucleotide positions for sequence data obtained at the cluster or feature. Thus, quality control can include determination of amplification errors, for example, based on presence or absence of mixed signals at a cluster, a threshold value for the statistical variation observed at one or more positions in the sequence data obtained for a cluster, a threshold value for the signal to noise ratio observed at one or more positions in the sequence data obtained for a cluster, a rate of decay in the signal to noise at a feature, or the like. Again this quality control data may be used to determine how well the fragment design was and/or to determine how to harvest the synthesized polynucleotides 26a, 26b, 26c, 26d or their amplification clusters.

Continuing with the exemplary embodiment of FIG. 1, after some or all of the synthesized polynucleotides 26a, 26b, 26c, 26d or their amplification clusters are harvested from the substrate 24, a fragment assembly phase 32 follows. In the fragment assembly phase 32, synthesized polynucleotides are assembled to generate one or more assembled polynucleotides targeting the target nucleic acid sequence 12. In the illustrated embodiment, the synthesized polynucleotides 26b, 26c, 26d are harvested from the substrate 24 while the synthesized polynucleotides 26a remain on the substrate 24. During the fragment assembly phase 32, the synthesized polynucleotides 26b, 26c, 26d are assembled to the synthesized polynucleotides 26a to generate assembled polynucleotides 34. As discussed in detail below, the assembly may be carried out in the presence of one or more enzymes, including but not limited to, DNA recombinase, beta protein, DNA polymerase, DNA ligase, circligase, or any combination thereof, for fragment assembly and gap repair.

The fragment assembly phase 32 can be followed by an assembly quality control phase 36 in which the assembled polynucleotides 34 are sequenced and the sequences of the assembled polynucleotides 34 are compared with the target nucleic acid sequence 12. In some embodiments, an amplification of the assembled polynucleotides 34 may be carried out before the sequencing, and sequencing runs may be carried out to the amplification clusters. In other embodiments, the amplification of the assembled polynucleotides 34 is optional. The sequencing runs in the assembly quality control phases 36 may be carried out similarly to the sequencing runs in the synthesis quality control phase 28. As illustrated, the sequencing runs may include utilizing a sequencing reagent 38 similar to the sequencing reagent 30. Quality control steps can be carried out for the assembled polynucleotide using techniques set forth above for nucleic acid fragments.

After the sequencing runs are carried out, a sequence of the assembled polynucleotides 34 or their amplification clusters may be obtained. By then comparing the sequence of the assembled polynucleotides 34, and/or their complementary sequence in the case of amplification clusters, with the sequence of the target nucleic acid sequence 12, a synthesis error rate may be determined. In some embodiments, a corresponding sequence accuracy score (e.g., by subtracting the error rate from one) may also be determined.

Similar to the synthesis quality control phase 28, the assembly quality control phase 36 may use the synthesis error rate for nucleic acid synthesis quality control. For example, the synthesis error rate determined by the sequencing in the assembly quality control phase 36 may be used to determine how well the fragment design was. By way of further example, a lower synthesis error rate of the assembled polynucleotides 34 or their amplification clusters may represent a better fragment design of the nucleic acid fragments 14a, 14b, 14c, 14d. Conversely, a higher synthesis error rate of the assembled polynucleotides 34 or their amplification clusters may represent a poorer fragment design of the nucleic acid fragments 14a, 14b, 14c, 14d. As such, a predetermined threshold of synthesis error rate may be set and used to compare with the synthesis error rate of the assembled polynucleotides 34 or their amplification clusters determined by the sequencing to determine whether the designed fragments are desirable. For example, the predetermined threshold error rate may be at most about 0.00%, 0.01%, 0.02%, 0.03%, 0.04%, 0.05%, 0.06%, 0.07%, 0.08%, 0.09%, 0.10%, 0.15%, 0.20%, 0.25%, 0.30%, 0.35%, 0.40%, 0.45%, 0.50%, 0.55%, 0.60%, 0.65%, 0.70%, 0.75%, 0.80%, 0.85%, 0.90%, 0.95%, 1.00%, 1.10%, 1.20%, 1.30%, 1.40%, 1.50%, 1.60%, 1.70%, 1.80%, 1.90%, 2.00%, 2.10%, 2.20%, 2.30%, 2.40%, 2.50%, 2.60%, 2.70%, 2.80%, 2.90%, 3.00%, 4.00%, 5.00%, 6.00%, 7.00%, 8.00%, 9.00%, 10.00%, 15.00%, 20.00%, 25.00%, 30.00%, 35.00%, 40.00%, 45.00%, 50.00%, 55.00%, 60.00%, 65.00%, 70.00%, 75.00%, 80.00%, 85.00%, 90.00%, 95.00%, 100%. This information can be used to design a different set of fragment sequences or different assembled polynucleotide. The synthesis and QC procedure can be repeated several times to allow iterative improvement in sequence quality.

In addition, the synthesis error rate determined by the sequencing in the assembly quality control phase 36 may be used to determine selective harvesting of the assembled polynucleotides 34 or their amplification clusters. For example, the assembled polynucleotides 34 or their amplification clusters may be selectively harvested when the error rate is equal to, less than, or higher than a predetermined threshold error rate. The predetermined threshold error rate may be at most about 0.00%, 0.01%, 0.02%, 0.03%, 0.04%, 0.05%, 0.06%, 0.07%, 0.08%, 0.09%, 0.10%, 0.15%, 0.20%, 0.25%, 0.30%, 0.35%, 0.40%, 0.45%, 0.50%, 0.55%, 0.60%, 0.65%, 0.70%, 0.75%, 0.80%, 0.85%, 0.90%, 0.95%, 1.00%, 1.10%, 1.20%, 1.30%, 1.40%, 1.50%, 1.60%, 1.70%, 1.80%, 1.90%, 2.00%, 2.10%, 2.20%, 2.30%, 2.40%, 2.50%, 2.60%, 2.70%, 2.80%, 2.90%, 3.00%, 4.00%, 5.00%, 6.00%, 7.00%, 8.00%, 9.00%, 10.00%, 15.00%, 20.00%, 25.00%, 30.00%, 35.00%, 40.00%, 45.00%, 50.00%, 55.00%, 60.00%, 65.00%, 70.00%, 75.00%, 80.00%, 85.00%, 90.00%, 95.00%, 100%. In some embodiments, the error rates of the assembled polynucleotides 34 or their amplification clusters may be compared, and those assembled polynucleotides that have the lowest, the highest, or equal to, less than, or higher than a predetermined threshold error rate may be selectively harvested. The assembled polynucleotides 34 may be harvested from the substrate 24 optically, chemically, magnetically, electrically, electromagnetically, or any combination thereof In some embodiments, the assembled polynucleotides 34 may be in turn used to create other nucleic acids, for example, via a transcription phase 40. For example, the assembled polynucleotides 34 may be DNA 42, which may be used as a template for synthesizing mRNA 44. The DNA can be single stranded or double stranded to suit particular uses. In certain embodiments, the transcription phase 40 may be followed by a translation phase 46. For example, the synthesized mRNAs 44 may be used as templates for synthesizing proteins 48. Transcription and translation can be carried out using methods known in the art such as those described in Sambrook, et al., Molecular Cloning: A Laboratory Manual (3rd Edition, 2001); Sambrook, et al., Molecular Cloning: A Laboratory Manual (2nd Edition, 1989); Maniatis et al., Molecular Cloning: A Laboratory Manual (1982); and Ausubel et al., Current Protocols in Molecular Biology (John Wiley and Sons, updated July 2008), each of which is incorporated herein by reference.

Figure 2:
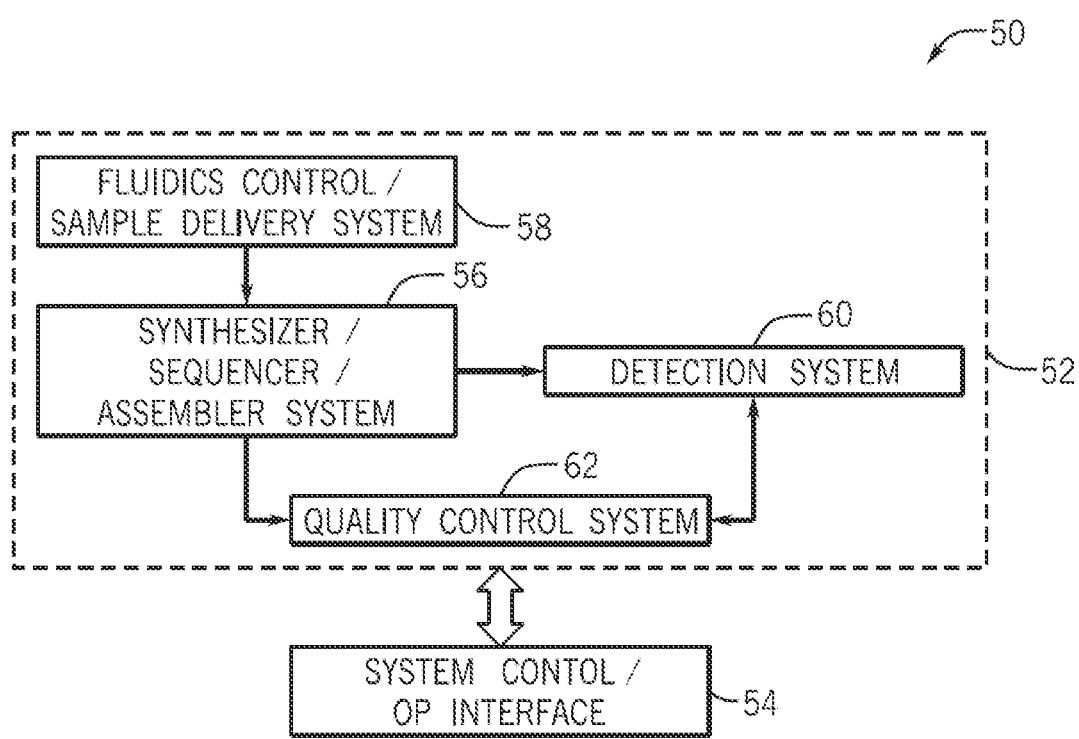
FIG. 2 is a block diagram of a system that may be used in conjunction with the technique of FIG. 1.

FIG. 2 is a block diagram of a synthesis system 50 that may be used in conjunction with the technique of FIG. 1 or other methods set forth herein. The synthesis system 50 includes a synthesizer 52 designed to synthesize nucleic acids. The synthesizer 52 communicates with a system control/operator interface 54. The system control/operator interface 54 may be used for fragment design based on the target nucleic acid sequence 12. For example, the system control/operator interface 54 may execute a program stored locally or remotely to facilitate designs of one or more nucleic acid fragments based on the target nucleic acid sequence 12, as noted above. Alternatively or additionally, a user may input one or more designed nucleic acid fragment sequences into the system control/operator interface 54.

The system control/operator interface 54 may include a general purpose or application-specific computer designed to monitor process parameters, acquired data, system settings, and so forth. The system control/operator interface 54 may include one or more processors and one or more memory devices storing instructions executable by the one or more processors. The operator interface may be generated by a program executed locally or by programs stored on and/or executed within synthesizer 52 to provide visual indications of the health of the systems or subsystems of the synthesizer 52, the quality of the data acquired, and so forth.

The system control/operator interface 54 may also permit a user to interface with the system to regulate operation, initiate and interrupt synthesis, evaluate quality control information, and any other interactions that may be desired with the system hardware or software. For example, the system control/operator interface 54 may automatically undertake and/or modify steps to be performed in a synthesis procedure, without input from a user. Alternatively or additionally, the system control/operator interface 54 may generate recommendations regarding steps to be performed in a synthesis procedure and display these recommendations to the user. This mode would allow for input from the human operator before undertaking and/or modifying steps in the sequencing procedure. In addition, the system control/operator interface 54 may provide an option to the user allowing the user to select certain steps in a synthesis procedure to be automatically performed by the synthesizer 52 while requiring input from the user before undertaking and/or modifying other steps. In any event, allowing both automated and user interactive modes may provide increased flexibility in performing the synthesis procedure. In addition, the combination of automation and human-controlled interaction may further allow for the synthesis system 50 capable of creating and modifying new sequencing procedures and algorithms through adaptive machine learning based on the inputs gathered from the user and/or subsystems of the synthesizer 52.

The system control/operator interface 54 may include a post-processing system that may include one or more programmed computers that receive detected information, which may be in the form of pixilated image data and derive sequence data from the image data. The post-processing system may include image recognition algorithms which distinguish between colors of dyes attached to nucleotides that bind at individual sites during sequencing processes (e.g., by analysis of the image data encoding specific colors or intensities), and logs the sequence of the nucleotides at the individual site locations. Progressively, then, the post-processing system may build sequence lists for the individual sites of the sample array which can be further processed to establish genetic information for extended lengths of material by various bioinformatics algorithms.

The synthesizer 52 includes a synthesizer/sequencer/assembler system 56 configured to carry out various steps of the technique illustrated in FIG. 1, including the fragment synthesis phase 22, the nucleic acid sequencing during the synthesis quality control phase 28 and the assembly quality control phase 36, and the fragment assembling phases 32. In certain embodiments, the synthesizer/sequencer/assembler system 56 is configured to carry out the transcription phase 40 and/or the translation phase 46 illustrated in FIG. 1. These phases are exemplary and it will be understood that the system can be configured to carry out additional or alternative phases. As discussed in detail below, one or more support systems (e.g., the substrate 24), including but not limited to, a bead, a magnetic bead, a glass slide, a microchip, a nano droplet, an electrowetting cartridge, or any combination thereof, may be used for the fragment synthesis phase 22, the synthesis quality control phases 28, the fragment assembly phase 32, and/or the assembly quality control phase 36 illustrated in FIG. 1. The support system may be used as a reaction container or carrier in conjunction with the synthesizer/sequencer/assembler system 56. The synthesizer/sequencer/assembler system 56 may be a single platform or substrate or may include multiple platforms or substrates, as appropriate. For example, fragment synthesis may occur on a first substrate while assembly may occur on a second substrate. Further, fragment synthesis and fragment assembly may involve substrates with different resolution (e.g., different molecule density resolution). In particular embodiments, for multiplatform synthesizer/sequencer/assembler, moving between the platforms may be automatic or may include certain operator-mediated steps.

The synthesizer 52 also includes a fluidics control/delivery system 58 and a detection system 60. The fluidics control/delivery system 58 may receive a plurality of process fluids for delivery to the synthesizer/sequencer/assembler system 56. As will be appreciated by those skilled in the art, the process fluids may vary depending upon the particular phases of nucleic acid synthesis and depending upon the synthetic protocol used. For example, in fragment synthesis phase 22, the process fluids may include a polymerase (e.g., TdT) and nucleotides of the four common DNA types. In sequencing (e.g., sequencing by synthesis, or SBS) of the synthesis quality control phase 28 and the assembly quality control phase 36, the process fluids may include a polymerase and tagged nucleotides of the four common DNA types. The nucleotides used in the sequencing phase may differ from those used in the synthesis phase by including labels such as unique fluorescent tags. The fluorescent tags allow the detection system 60 to detect which nucleotides were last added to probes hybridized to template nucleic acids at individual sites of the substrate 24. Nucleotides used in one or both of the synthesis and sequencing phases can include reversible blocking moieties. The reversible blocking moieties prevent addition of more than one nucleotide per cycle of synthesis or sequencing, respectively. In other sequencing methods, such as sequencing by ligation, the process fluids may include query oligonucleotide probes with unique fluorescent tags attached thereto. Similarly, the query probes will bind to the templates at each site in a configuration that allows ligation of the query probes to an anchor primer and may be detected by the detection system 60 for sequencing of the templates at each site.

In some embodiments, the fluidics control/delivery system 58 may deliver to the synthesizer/sequencer/assembler system 56 a plurality of process fluids at various times. For example, during the sequencing, the fluidics control/delivery system 58 may, after delivering the process fluids including a polymerase and tagged nucleotides of the four common types found naturally in DNA, deliver process fluids that include reagents for removing reversible blocking moieties from nucleotides, cleaving nucleotide linkers, or for removing bases from ligated oligonucleotides to release a newly extendable probe terminus. Exemplary fluidic and detection configurations that can be used in the methods and devices set forth herein are described in WO 07/123744; US Pat App. Pub. Nos. 2012/0270305 A1; 2013/0023422 A1; and 2013/0260372 A1; and U.S. Pat. Nos. 5,528,050; 5,719,391; 8,158,926 and 8,241,573, each of which is incorporated herein by reference. In particular embodiments commercially available sequencing platforms can be modified to carry out a nucleic acid "writing" function, as set forth herein, in addition to the sequencing (i.e. "reading") function. Exemplary platforms include, but are not limited to HiSeq®, MiSeq® and NextSeq™ platforms (Illumina, Inc. San Diego, CA), SOLiD® and Ion Torrent® platforms (Thermo Fisher, Waltham, MA); pyrosequencing platforms (Roche, Basel Switzerland), and nanopore platforms (Oxford Nanopore, Oxford England). As provided herein, the fluidics control/delivery system 58 may control delivery of sequencing reagents based on whether the system 50 determines that the synthesis phase is complete (e.g., via signals generated by nucleotide incorporation and detected by the synthesizer/sequencer/assembler system 56) or whether the system 50 determines that a sufficient quality product has resulted from the synthesis phase. Alternatively, the fluidics control/delivery system 58 may reinitiate all or part of a synthesis protocol for creating new nucleic acid fragments and/or new assembled polynucleotides.

As noted above, in some embodiments, the synthesized polynucleotides (e.g., the synthesized polynucleotides 26*a*, 26*b*, 26*c*, 26*d*, the assembled polynucleotides 34) may be amplified on the substrate 24 before sequencing. This process may include amplification of fragments of DNA or RNA on a support to create a multitude of sites of DNA or RNA fragments the sequence of which are determined by the sequencing process. Exemplary methods for producing sites of amplified nucleic acids suitable for sequencing include, but are not limited to, rolling circle amplification (RCA) (Lizardi et al., Nat. Genet. 19:225-232 (1998)), bridge amplification (Adams and Kron, Method for Performing Amplification of Nucleic Acid with Two Primers Bound to a Single Solid Support, Mosaic Technologies, Inc. (Winter Hill, MA); Whitehead Institute for Biomedical Research, Cambridge, MA, (1997); Adessi et al., Nucl. Acids Res. 28:E87 (2000); Pemov et al., Nucl. Acids Res. 33:e11(2005); or U.S. Pat. No. 5,641,658), polony generation (Mitra et al., Proc. Natl. Acad. Sci. USA 100:5926-5931 (2003); Mitra et al., Anal. Biochem. 320:55-65(2003)), or clonal amplification on beads using emulsions (Dressman et al., Proc. Natl. Acad. Sci. USA 100:8817-8822 (2003)) or ligation to bead-based adapter libraries (Brenner et al., Nat. Biotechnol. 18:630-634 (2000); Brenner et al., Proc. Natl. Acad. Sci. USA 97:1665-1670 (2000)); Reinartz, et al., Brief Funct. Genomic Proteomic 1:95-104 (2002)).

The synthesizer 52 also includes a quality control system 62. The quality of samples (e.g., the synthesized polynucleotides 26*a*, 26*b*, 26*c*, 26*d*, the assembled polynucleotides 34), the quality of the data derived by the synthesis system 50, and the various parameters used for processing the samples (e.g., sequencing) may be assessed and/or controlled by the quality control system 26. For example, as noted above, the quality control system may receive sequencing information and may determine a synthesis error rate and/or the yield of a predetermined synthesized sequence and/or the yield of synthesized sequences with a predetermined error rate, which in turn may be used by the quality control system 62 to determine how well the fragment was designed and/or to determine harvesting of the synthesized and/or assembled polynucleotides (e.g., which cluster to harvest). In certain embodiments, the quality control system 62 may communicate with the system control/operator interface 54 to provide feedback to the fragment design phases 10 so that an adaptive fragment design may be carried out, either automatically or by a user. The quality control system 62 may include one or more programmed processors, or general purpose or application-specific computers which communicate with sensors and other processing systems within the fluidics control/sample delivery system 58, the synthesizer/sequencer/assembler system 56, and the detection system 62.

Figure 3:
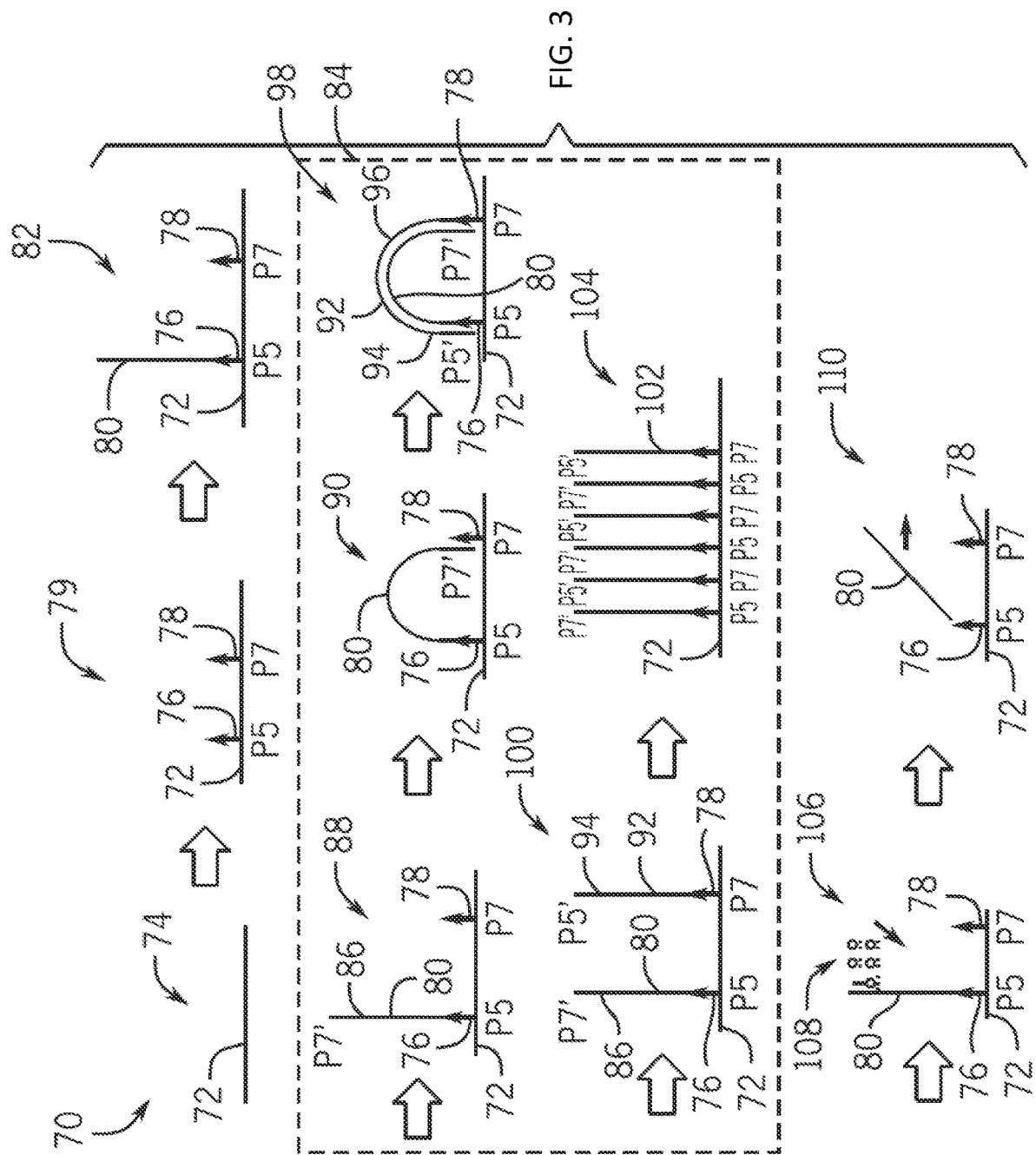
FIG. 3 is a fragment synthesis technique for generating a template-independent single-stranded polynucleotide fragment of a synthetic polynucleotide molecule with sequencing feedback according to embodiments of the present disclosure.

FIG. 3 illustrates a fragment synthesis technique 70 for generating a template-independent single-stranded polynucleotide fragment of a synthetic polynucleotide molecule with sequencing feedback according to embodiments of the present disclosure. It should be noted that although single-stranded polynucleotide is illustrated in FIG. 3, double-stranded polynucleotide is also contemplated in the fragment synthesis technique 70 described herein. The fragment synthesis technique 70 starts with a substrate 72 (e.g., the substrate 24 of FIG. 1) (phase 74).

The substrate 72 may be modified such that a plurality of primers (e.g., a P5 primer 76, a P7 primer 78) is immobilized on a surface of the substrate 72 (phase 79). P5 and P7 primers are described in U.S. Pat. No. 8,563,477 and Bentley et al., Nature 456:53-59 (2008), each of which is incorporated herein by reference. Although one copy of the P5 primer 76 and one copy of the P7 primer 78 are illustrated in FIG. 3, it should be noted that multiple copies of the P5 primer 76 and the P7 primer 78, or multiple copies of other suitable primers, may be immobilized on the substrate 72. As discussed in detail below, the density of the primers on the substrate 72 may be controlled.

Nucleic acid synthesis can be carried out on the 3' end of the P5 primer. The nucleic acid synthesis of a single-stranded polynucleotide fragment is based on the sequence of a fragment of a nucleic acid target. As such, a series of individual nucleotides may be flowed sequentially on the substrate 72 such that the individual nucleotides are incorporated successively onto the 3' end of the P5 primer 76 to generate an extended polynucleotide 80 (phase 82). The order of delivery for the individual nucleotide types is based on the sequence of the nucleic acid fragment target (e.g., from a 5' end to a 3' end) or the complement thereof. Because the extended polynucleotide 80 is synthesized without a template strand, this synthesis may be referred to as template-independent synthesis. As noted above, the synthesis of the extended polynucleotide 80 may be carried out in the presence of a polymerase, such as TdT. Furthermore, the nucleotides can be analogs having a reversible blocking moiety to prevent incorporation of more than one nucleotide to the primer per cycle. In this case a cycle can include a step of removing the blocking moiety from the extended primer to regenerate a 3' oxygen that is capable of incorporating a new nucleotide analog in a subsequent cycle.

In some embodiments, synthesis of the single-stranded polynucleotide fragment may be carried out on the 3' end of a cleavable adapter instead of the P5 primer 76. For example, the cleavable adapter may include a complementary sequence of the P5 primer 76 (e.g., a P5' adapter) such that the cleavable adapter may be hybridized to the immobilized P5 primer 76. As such, the cleavable adapter is also immobilized to the substrate 72. Similar to the synthesis illustrated above with respect to the extension of the 3' end of the P5 primer 76, the synthesis may be carried out on the 3' end of the cleavable adapter to generate the extended polynucleotide 80. As exemplified previously herein, other nucleic acid synthesis methods can be used to create nucleic acid fragments, including, but not limited to known chemical synthesis methods.

After the extended polynucleotide 80 is synthesized on the substrate 72, a quality control phase (e.g., the synthesis quality control phase 28 in FIG. 1) may be carried out. As noted above, in certain embodiments, the extended polynucleotide 80 may be amplified before the quality control phase. One example of such amplification 84 is illustrated in FIG. 3 with a dashed box, representing an optional phase. Other phases can be optional for some embodiments.

As illustrated, the amplification 82 of the extended polynucleotide 80 may be by bridge amplification. For example, a P7' adapter 86 may be ligated to the 3' end of the extended polynucleotide 80 (phase 88). The P7' adapter 86 comprises a sequence complementary to a sequence of the P7 primer 78. The single-stranded extended polynucleotide 80 may be bridged over such that the P7' adapter 86 may be hybridized with the P7 primer 78 immobilized on the substrate 72 (phase 90). A second strand 92 extending from a 3' end of the P7 primer 78 may be synthesized using the extended polynucleotide 80 and the P7' adapter 86 as a template (phase 98). As such, a double stranded nucleic acid 96 is formed including the extended polynucleotide 80 and the complementary second strand 92. The 3' end of the second strand 92 may include a P5' adapter 94 that is complementary to the P5 primer 76. The double stranded nucleic acid 96 may then be denatured so that two single-stranded polynucleotides (e.g., the extended polynucleotide 80, and the second strand 92) may be formed with one end of each of the two single-stranded polynucleotides attached to the substrate 72 (phase 100). The amplification steps may be repeated and an amplification cluster 102 of the extended polynucleotide 80 may be formed on the substrate 72 (phase 104).

Regardless of whether amplification 84 of the extended polynucleotide 80 is carried out, the extended polynucleotide 80 can be sequenced (phase 106). In the illustrated embodiment, the sequencing may be a sequencing by synthesis, or SBS, technique in which tagged nucleotides 108 of the four common DNA/RNA types may be flowed on the substrate. Each of the tagged nucleotides 108 can have a unique fluorescent tag and a reversible blocking moiety linked to it. The fluorescent tag allows a detection system (e.g., the detection system 60 of FIG. 2) to detect which nucleotides were last added to probes hybridized to the template nucleic acid (e.g., the extended polynucleotide 80) at individual sites on the substrate 72. The reversible blocking moiety prevents addition of more than one nucleotide per cycle at each site. As discussed in detail below, the sequencing of the extended polynucleotide 80 may be carried out with any other suitable methods, including sequencing by ligation, pyrosequencing, sequencing via hydrogen ion detection, nanopore sequencing or the like.

Nucleic acids made by methods set forth herein can be sequenced by providing, different nucleotides (or oligonucleotides) to an array of features each having a synthesized nucleic acid so as to produce different signals at each feature, each signal corresponding to a specific species of nucleotide (or oligonucleotide) that has been added to the feature. For example, in a case where four different labels are used, corresponding to four different species of nucleotide (or oligonucleotide), individual images can be acquired, wherein each image captures a single color (or other signal type) among the four possible colors (or signal types). In this example, the signal color is different for each of the four different images, thereby producing a cycle of four color images that corresponds to the four possible nucleotides present at a particular position in the nucleic acid. In certain aspects, such methods can further include providing additional labeled nucleotides (or oligonucleotides) to the array of molecules, thereby producing a plurality of cycles of color images. Some exemplary sequencing techniques that produce images from multiple cycles, and often multiple images per cycle, are set forth below in further detail.

SBS techniques generally involve the enzymatic extension of a nascent nucleic acid strand through the iterative addition of nucleotides against a template strand. In traditional methods of SBS, a single nucleotide monomer may be provided to target nucleic acids in the presence of a polymerase in each delivery step. However, in the methods described herein, more than one type of nucleotide monomer can be provided to a target nucleic acid in the presence of a polymerase in each of the delivery steps.

SBS can utilize nucleotide monomers that have a terminator moiety or those that lack any terminator moieties. Methods utilizing nucleotide monomers lacking terminators include, for example, pyrosequencing and sequencing using gamma-phosphate-labeled nucleotides, as set forth in further detail below. In methods using nucleotide monomers lacking terminators, the number of nucleotides added to a nascent nucleic acid strand by polymerase in each cycle is generally variable and dependent upon the template sequence and the mode of nucleotide delivery. For SBS techniques that utilize nucleotide monomers having a terminator moiety, the terminator can be effectively irreversible under the sequencing conditions used, as is the case for traditional Sanger sequencing which utilizes dideoxynucleotides, or the terminator can be reversible as is the case for sequencing methods commercially available from Illumina, Inc. (San Diego, CA) or described in Bentley et al., Nature 456:53-59 (2008), WO 04/018497; WO 91/06678; WO 07/123744; U.S. Pat. Nos. 7,057,026; 7,329,492; 7,211,414; 7,315,019 or 7,405,281, and US Pat. App. Pub. No. 2008/0108082 A1, each of which is incorporated herein by reference.

Alternatively or additionally to the use of terminator moieties, SBS techniques can utilize nucleotide monomers that have a label moiety or those that lack a label moiety. Accordingly, incorporation events can be detected based on a characteristic of the label, such as fluorescence of the label; a characteristic of the nucleotide monomer such as molecular weight or charge; a byproduct of incorporation of the nucleotide, such as release of hydrogen or pyrophosphate; or the like. In embodiments, where two or more different nucleotides are simultaneously present in a sequencing reagent or extended nucleic acid, the different nucleotides can be distinguishable from each other. For example, the different nucleotides present in a sequencing reagent or extension product can have different labels and they can be distinguished using appropriate optics as exemplified by the sequencing platforms commercially available from Illumina, Inc. (San Diego, CA) or described in US Pat App. Pub. Nos. 2012/0270305 A1; 2013/0023422 A1; and 2013/0260372 A1; and U.S. Pat. Nos. 5,528,050; 5,719,391; 8,158,926 and 8,241,573, each of which is incorporated herein by reference.

Preferably in reversible terminator-based sequencing embodiments, the labels do not substantially inhibit extension under SBS reaction conditions. However, the detection labels can be removable, for example, by cleavage or degradation. Images can be captured following incorporation of labels into arrayed features of synthesized nucleic acids (e.g. nucleic acid fragments or assembled nucleic acids). In particular embodiments, each cycle involves simultaneous delivery of four different nucleotide types to the array and each nucleotide type has a spectrally distinct label. Four images can then be obtained, each using a detection channel that is selective for one of the four different labels. Alternatively, different nucleotide types can be added sequentially and an image of the array can be obtained between each addition step. In either embodiment each image will show nucleic acid features that have incorporated nucleotides of a particular type. Different features will be present or absent in the different images due the different sequence content of each feature. However, the relative position of the features will remain unchanged in the images. Images obtained from such reversible terminator-SBS methods can be stored, processed and analyzed as set forth herein. Following the image capture step, labels can be removed and reversible terminator moieties can be removed for subsequent cycles of nucleotide addition and detection. Removal of the labels after they have been detected in a particular cycle and prior to a subsequent cycle can provide the advantage of reducing background signal and crosstalk between cycles.

Additional exemplary SBS systems and methods which can be utilized with the methods and systems described herein are described in U.S. Pat. App. Pub. No. 2007/0166705, U.S. Pat. App. Pub. No. 2006/0188901, U.S. Pat. No. 7,057,026, U.S. Pat. App. Pub. No. 2006/0240439, U.S. Pat. App. Pub. No. 2006/0281109, PCT Publication No. WO 05/065814, U.S. Pat. App. Pub. No. 2005/0100900, PCT Publication No. WO 06/064199 and PCT Publication No. WO 07/010,251, the disclosures of which are incorporated herein by reference.

Particular sequencing embodiments can utilize pyrosequencing techniques. Pyrosequencing detects the release of inorganic pyrophosphate (PPi) as particular nucleotides are incorporated into the nascent strand (Ronaghi et al. (1996) Analytical Biochemistry 242(1), 84-9; Ronaghi, M. (2001) Genome Res. 11(1), 3-11; Ronaghi et al. (1998) Science 281(5375), 363; U.S. Pat. Nos. 6,210,891; 6,258,568 and 6,274,320, the disclosures of which are incorporated herein by reference). In pyrosequencing, released PPi can be detected by being converted to adenosine triphosphate (ATP) by ATP sulfurylase, and the level of ATP generated can be detected via luciferase-produced photons. Synthesized nucleic acids (e.g. fragments or assembled nucleic acids) can be attached at respective features in an array and the array can be imaged to capture the chemiluminescent signals that are produced due to incorporation of nucleotides at the features of the array. An image can be obtained after the array is treated with a particular nucleotide type (e.g. A, T, C or G). Images obtained after addition of each nucleotide type will differ with regard to which features in the array are detected. These differences in the image reflect the different sequence content of the features on the array. However, as with other SBS methods the relative locations of each feature will remain unchanged in the images. The images can be analyzed using the systems and methods set forth herein. For example, images obtained after treatment of the array with each different nucleotide type can be handled in the same way as exemplified herein for images obtained for reversible terminator-based sequencing methods.

Pyrophosphate detection can be used to monitor synthesis of nucleic acids in real-time. For example, a TdT based synthesis method can be used to synthesize nucleic acid fragments, as set forth above. As each nucleotide is added a pyrophosphate will be released. The amount of pyrophosphate released in each synthesis cycle can be detected and quantified to determine yield and efficiency of the synthesis. In this way, pyrophosphate detection can be evaluated similarly to how DMT is evaluated in chemical synthesis.

Some embodiments involve sequencing by ligation techniques. Such techniques utilize DNA ligase to incorporate oligonucleotides and then the incorporated oligonucleotides can be identified. The oligonucleotides typically have different labels that are correlated with the identity of a particular nucleotide in a sequence to which the oligonucleotides hybridize. As with other SBS methods, an array of features to which nucleic acid fragments or assembled nucleic acids are attached can be used and images can be obtained following treatment of the array with the labeled sequencing reagents. Each image will show nucleic acid features that have incorporated labels of a particular type. Different features will be present or absent in the different images due the different sequence content of each feature, but the relative position of the features will remain unchanged in the images. Images obtained from ligation-based sequencing methods can be stored, processed and analyzed as set forth herein. Exemplary sequencing by ligation systems and methods which can be utilized with the methods and systems described herein are described in U.S. Pat. Nos. 6,969,488, 6,172,218, and 6,306,597, the disclosures of which are incorporated herein by reference.

It will be appreciated that any of the above-described sequencing processes can be incorporated into the methods and/or systems described herein. Furthermore, it will be appreciated that other known sequencing processes can be readily modified for use with the methods and/or systems described herein. After the sequencing of the extended polynucleotide 80, a sequence of the extended polynucleotide 80 is evaluated. When the sequence of the extended polynucleotide 80 is compared with the sequence of the target nucleic acid, a synthesis error rate may be obtained as illustrated above. Also as illustrated above, a yield of a predetermined synthesized sequence (e.g., an error free sequence) and/or a yield of synthesized sequences with a predetermined error rate (e.g., when the amplified cluster of the extended polynucleotide 80 present) may be obtained. Such yield and/or the synthesis error rate may be used for nucleic acid synthesis quality control (e.g., the synthesis quality control phase 28 of FIG. 1), for example, to determine how well the fragment design was and/or to determine how to harvest the extended polynucleotide 80. For example, based on the error rate and/or yield, the extended polynucleotide 80 may or may not be cleaved from the substrate 72. In the illustrated embodiment, the extended polynucleotide 80 is cleaved from the P5 primer 76 (phase 110).

Figure 4:
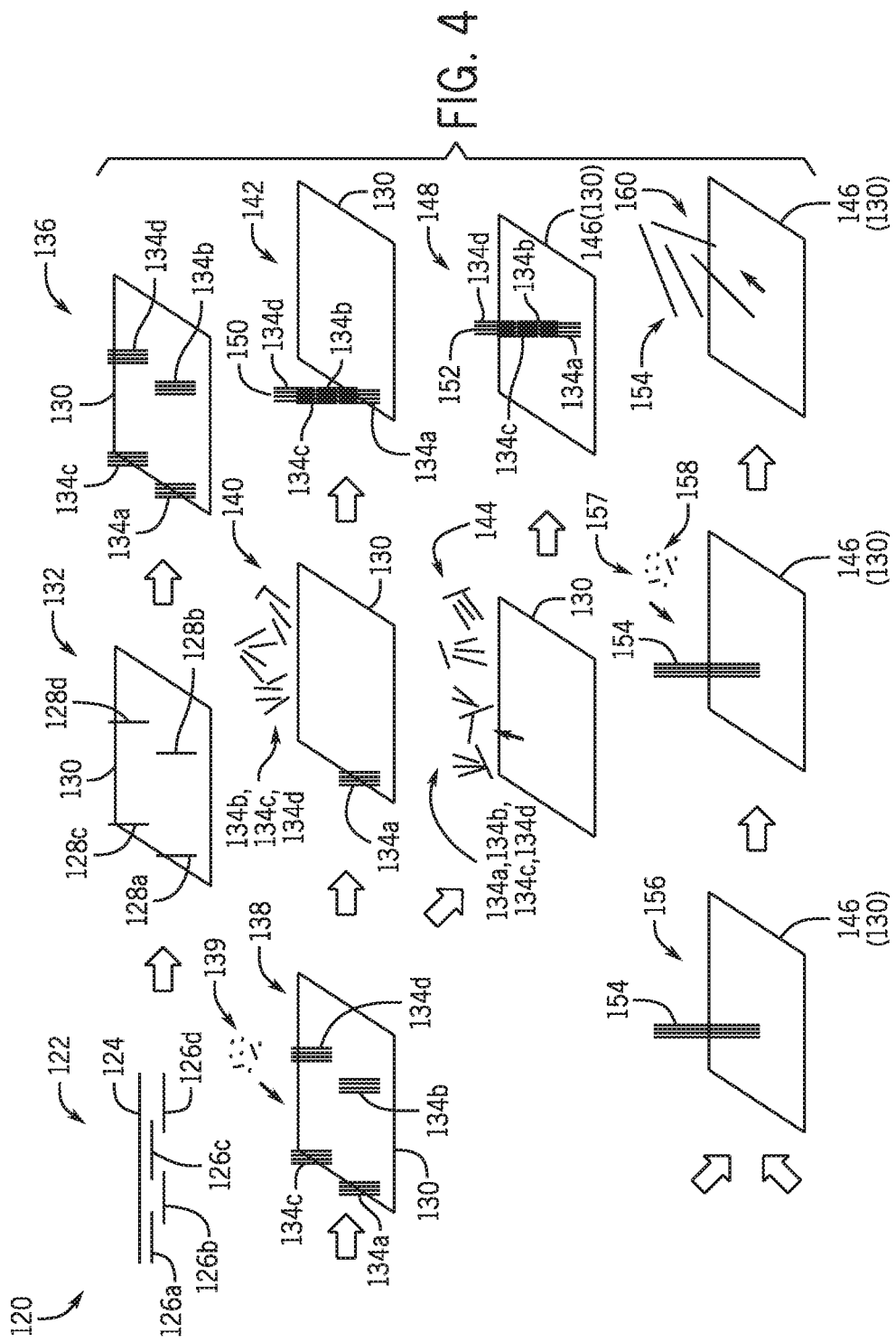
FIG. 4 is a fragment synthesis and assembly technique for assembling multiple polynucleotide fragments of a synthetic polynucleotide molecule with sequencing feedback for the fragments and the assembled synthetic polynucleotide according to embodiments of the present disclosure.

FIG. 4 illustrates a fragment synthesis and assembly technique 120 for assembling multiple polynucleotide fragments of a synthetic polynucleotide molecule with sequencing feedback for the fragments and the assembled synthetic polynucleotide according to embodiments of the present disclosure. The fragment synthesis and assembly technique 120 may start with a fragment design phase 122 (e.g., the fragment design phase 10 illustrated in FIG. 1). The fragment design phase 122 may include using a target nucleic acid 124 to design sequences for one or more nucleic acid fragments (e.g., fragments 126a, 126b, 126c, 126d). Although four nucleic acid fragments (e.g., fragments 126a, 126b, 126c, 126d) are illustrated in FIG. 4, it is understood that any number (e.g., 1, 2, 3, 4, 5, 6, 7, 8, 9, 10, or more) of nucleic acid fragment sequences may be designed based on the target nucleic acid sequence 124. The nucleic acid fragments 126a, 126b, 126c, 126d may be designed the same as or similarly to the process illustrated by the fragment design phase 10 of FIG. 1. Furthermore, each of the nucleic acid fragments 126a, 126b, 126c, 126d may undergo the same or similar synthesis and sequencing processes as illustrated in FIG. 3 with respect to an individual single-stranded nucleic acid fragment.

Based on the sequence of each of the nucleic acid fragments 126a, 126b, 126c, 126d, a corresponding polynucleotide 128a, 128b, 128c, 128d may be synthesized on a substrate 130 (phase 132). The synthesized polynucleotides 128a, 128b, 128c, 128d correspond to the nucleic acid fragments 126a, 126b, 126c, 126d, respectively. The synthesis of the synthesized polynucleotides 128a, 128b, 128c, 128d may be the same as or similar to the synthesis of the extended polynucleotide 80 of FIG. 3. In some embodiments, the synthesized polynucleotides 128a, 128b, 128c, 128d may be amplified to generate the corresponding amplification clusters 134a, 134b, 134c, 134d on the substrate 130 (phase 136). In certain embodiments, such amplification is optional. The following phases, although exemplified for amplification clusters 134a, 134b, 134c, 134d, may be carried out on the synthesized polynucleotides 128a, 128b, 128c, 128d.

The amplification clusters 134a, 134b, 134c, 134d may be sequenced in parallel or sequentially in the presence of one or more sequencing reagents 139 (phase 138). As discussed above, synthesis error rates and/or yields (or amplification error rates and/or yields) with respect to the amplification clusters 134a, 134b, 134c, 134d may be obtained from the sequencing. In some embodiments, the synthesis (or amplification) error rates and/or the yields may be used to provide feedback to the fragment design phase 122 to determine how well the fragment design was. In certain embodiments, a plurality of cycles of such feedback may be provided so that an adaptive fragment design routine may be carried out, automatically or by a user.

When the fragment design is determined to be desirable, one or more of the amplification clusters 134a, 134b, 134c, 134d may be harvested from the substrate 130. In some embodiments, the first amplification cluster (e.g., the amplification cluster 134a) is not harvested from the substrate 130 while other amplification clusters (e.g., the amplification clusters 134b, 134c, 134d) are harvested (phase 140). In such cases, the amplification clusters 134a, 134b, 134c, 134d may be assembled on a substrate 130 to generate assembled polynucleotides 150 (phase 142). In other embodiments, all of the amplification clusters 134a, 134b, 134c, 134d are harvested from the substrate 130 (phase 144)). In such cases, the amplification clusters 134a, 134b, 134c, 134d may be assembled on a different substrate 146 or the same substrate 130 to generate assembled polynucleotides 152 (phase 148).

As discussed above, synthesis (or amplification) error rates and/or yields with respect to the amplification clusters 134a, 134b, 134c, 134d may be used to determine how the amplification clusters 134a, 134b, 134c, 134d are harvested. For example, all or a part of each of the amplification clusters 134a, 134b, 134c, 134d may be harvested based on the synthesis error rates and/or the yields.

Regardless of how the amplification clusters 134a, 134b, 134c, 134d may be harvested and assembled, the assembled polynucleotides 150 or 152 may be processed for gap repairing to generate an assembled polynucleotide cluster 154 attached on the substrate 130 or 146 (phase 156). An assembly quality control phase 158 may follow the fragment assembly. As illustrated, the assembled polynucleotide cluster 154 may then be sequenced in the presence of one or more sequencing reagents 157 during an assembly quality control phase 158. Similarly, synthesis (or amplification) error rates and/or yields with respect to the assembled polynucleotide cluster 154 may be obtained from the sequencing. In some embodiments, the synthesis (or amplification) error rates and/or the yields may be used to provide feedback to the fragment design phase 122 to determine how well the fragment design was. In certain embodiments, a plurality of cycles of such feedback may be provided so that an adaptive fragment design routine may be carried out, automatically or by a user.

When the fragment design is determined to be desirable, all or a part of the assembled polynucleotide cluster 154 may be harvested from the substrate 130 or 146 (phase 160). The harvesting may be based on the synthesis (or amplification) error rates and/or yields with respect to the assembled polynucleotide cluster 154.

Figure 5:
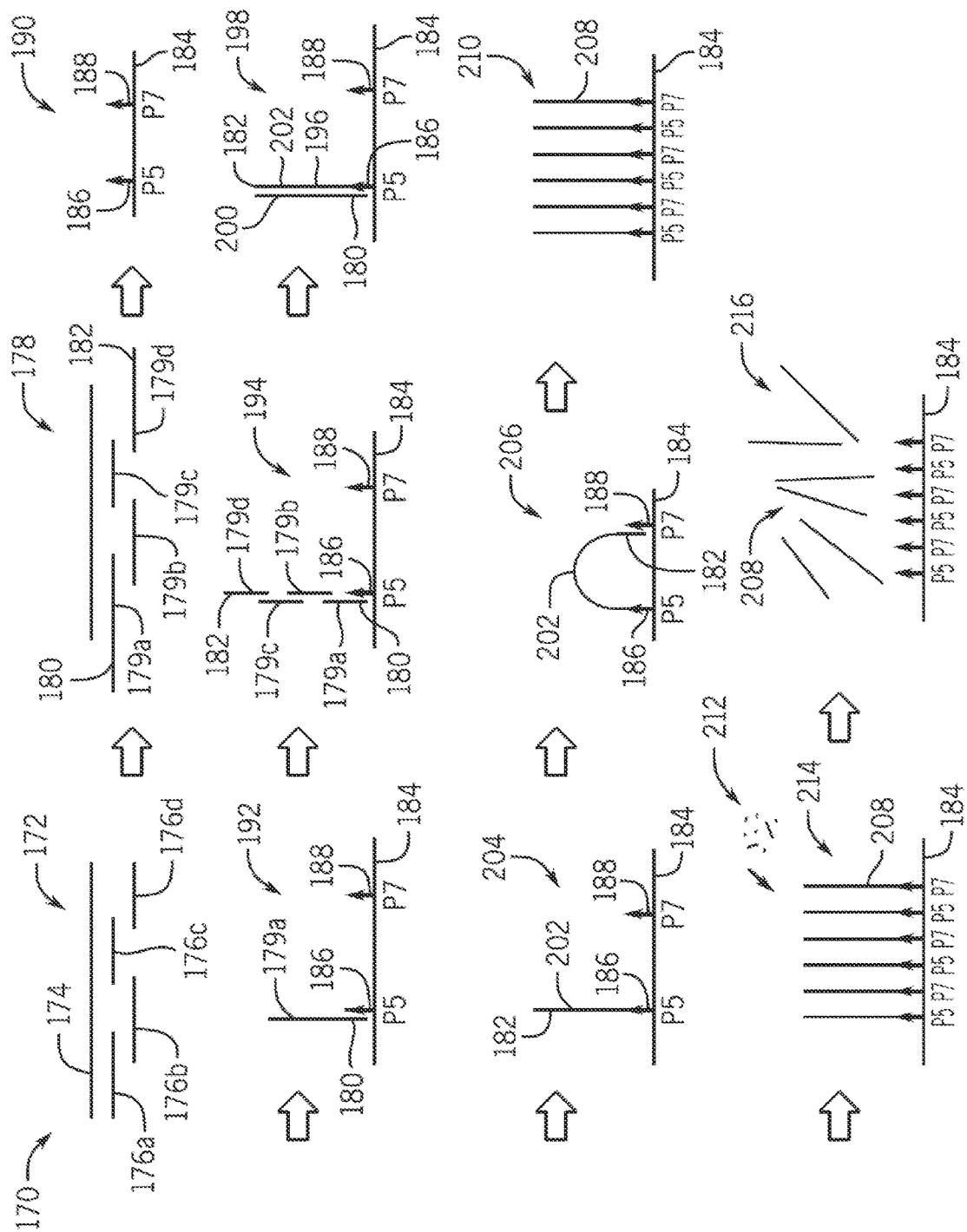
FIG. 5 is a polynucleotide fragment assembly technique with sequencing feedback according to embodiments of the present disclosure.

FIG. 5 illustrates a polynucleotide fragment assembly technique 170 with sequencing feedback according to embodiments of the present disclosure. The polynucleotide fragment assembly technique 170 may start with a fragment design phase 172 (e.g., the fragment design phase 10 illustrated in FIG. 1). The fragment design phase 172 may include using a target nucleic acid 174 to design one or more nucleic acid fragments (e.g., fragments 176a, 176b, 176c, 176d). Although four nucleic acid fragments (e.g., fragments 176a, 176b, 176c, 176d) are illustrated in FIG. 5, it is understood that any number (e.g., at least 1, 2, 3, 4, 5, 6, 7, 8, 9, 10, or more) of nucleic acid fragments may be designed based on the target nucleic acid sequence 174. The nucleic acid fragments 176a, 176b, 176c, 176d may be designed the same as or similarly to the process illustrated by the fragment design phase 10 of FIG. 1.

Based on the designed four nucleic acid fragments 176a, 176b, 176c, 176d, corresponding nucleic acid fragments 179a, 179b, 179c, 179d may be synthesized. For example, the synthesized nucleic acid fragments 179a, 179b, 179c, 179d target the designed nucleic acid fragments 176a, 176b, 176c, 176d, respectively. The synthesis of the nucleic acid fragments 179a, 179b, 179c, 179d may be carried out in any suitable manner, including the methods described in connection with FIG. 4. In addition, the first nucleic acid fragment 179a and the last nucleic acid fragment 179d may be further modified (phase 178). As illustrated, a cleavable adapter 180 may be ligated to a 5' end of the first nucleic acid fragment 179a, and a cleavable adapter 182 may be ligated to a 3' end of the last nucleic acid fragment 179d. The cleavable adapters 180, 182 may be any suitable adapters that have complementary sequences to primers that may be immobilized to a substrate 184. For example, as noted above, a P5 primer 186 and a P7 primer 188 may be immobilized to the substrate 184. As such, the cleavable adapter 180 may have a sequence of P5' that is complementary to the sequence of the P5 primer 186, and the cleavable adapter 182 may have a sequence of P7' that is complementary to the sequence of the P7 primer 188.

The synthesized nucleic acid fragments 179a, 179b, 179c, 179d may then be flowed on the substrate 184 in parallel or sequentially (phase 192). Because the cleavable adapter 180 on the 5' end of the nucleic acid fragment 179a is complementary to the P5 primer 186 immobilized on the substrate 184, the nucleic acid fragment 179a may be hybridized with the P5 primer 186 so that the nucleic acid fragment 179a is attached to the substrate 184. Other nucleic acid fragments 179b, 179c, 179d may then be assembled to the nucleic acid fragment 179a (phase 194). The assembly of the nucleic acid fragments 179a, 179b, 179c, 179d may be carried out in the presence of any suitable enzymes, including but limited to, DNA recombinase, beta protein, or any combination thereof.

Following the fragment assembly phase 194, the assembled nucleic acid fragments 179a, 179b, 179c, 179d may be repaired to generate a double-stranded polynucleotide 196 (phase 198). For example, the gaps between the nucleic acid fragments on each single strand 200 or 202 may be filled using the other single strand 202 or 200 as template. The fragment repair phase 198 may be carried out in the presence of any suitable enzymes, including but not limited to, DNA polymerase, DNA ligase, circligase, or any combination thereof.

The double-stranded polynucleotide 196 may then be denatured (phase 204). Because the strand 200 is hybridized with the other strand 202 that is immobilized to the substrate 184, the strand 200 may be washed away from the substrate 184 upon denaturation, and the strand 202 remain on the substrate 184. The strand 202 may then be amplified. For example, as illustrated, the strand 202 may undergo a bridge amplification in which the cleavable adapter 182 is hybridized with the P7 primer 188 (phase 206), and then a second strand may be synthesized using the strand 202 as a template to generate a double-stranded polynucleotide (e.g., similar to phase 98 illustrated in FIG. 3). The amplification of the strand 202 may also be carried out using rolling circle amplification (RCA), or any other suitable solid-phase amplification methods as noted above. As a result of the amplification, an amplification cluster 208 of the strand 202, including copies of the strand 202 and its complementary sequence, may be formed on the substrate 184 (phase 210). In some embodiments, such amplification phase (e.g., phases 206, 210) is optional.

The amplification cluster 208 may then be sequenced in the presence of one or more sequencing reagents 212 during an assembly quality control phase 214. Similarly as above, synthesis (or amplification) error rates and/or yields with respect to the amplification cluster 208 may be obtained from the sequencing. In some embodiments, the synthesis (or amplification) error rates and/or the yields may be used to provide feedback to the fragment design phase 172 to determine how well the fragment design was. In certain embodiments, a plurality of cycles of such feedback may be provided so that an adaptive fragment design routine may be carried out, automatically or by a user.

When the fragment design is determined to be desirable, all or a part of the amplification cluster 208 may be harvested from the substrate 184 (phase 216). The harvesting may be based on the synthesis error rates and/or yields with respect to the assembled polynucleotide cluster 154. As illustrated, the amplification cluster 208 may be cleaved from the P5 and P5 primers on the substrate 184.

Figure 6:
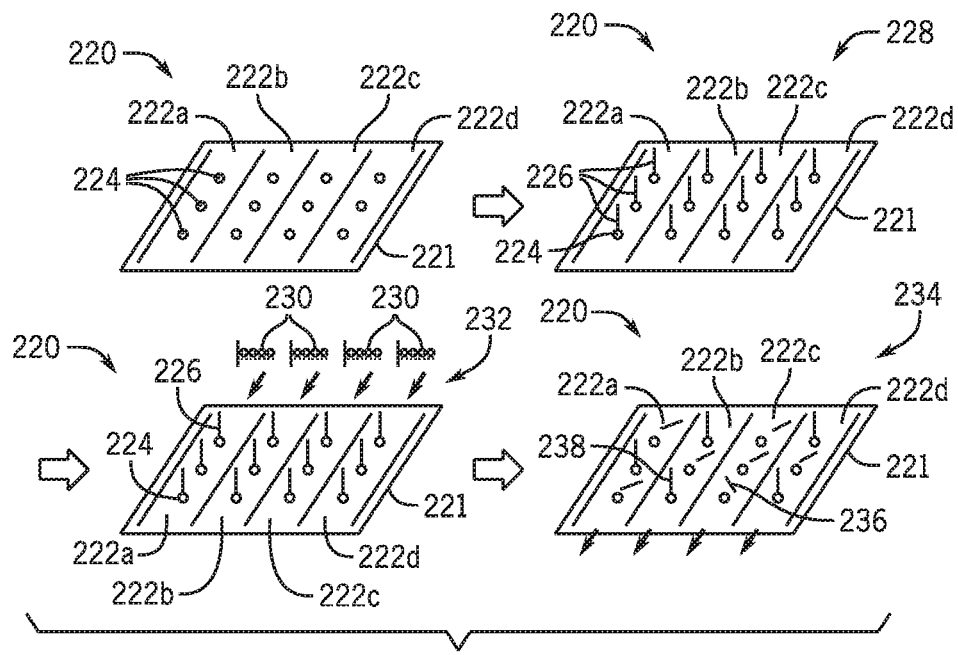
FIG. 6 is a flow cell for synthesizing different polynucleotide fragment sequences in parallel for later assembly into a synthetic polynucleotide molecule according to embodiments of the present disclosure.

FIG. 6 illustrates a flow cell 220 for synthesizing different polynucleotide fragment sequences in parallel for later assembly into a synthetic polynucleotide molecule according to embodiments of the present disclosure. The flow cell 220 includes a substrate 221 and one or more flow channels (e.g., flow channels 222a, 222b, 222c, 222d) in which various carrier fluids, reagents, and so forth may be introduced. Although four flow channels are illustrated in FIG. 6, it is understood that the flow cell 220 may include any number of flow channels (e.g., 1, 2, 3, 4, 5, 6, 7, 8, 9, 10, or more).

Each of the flow channels 222a, 222b, 222c, 222d may include on the substrate 221 one or more reaction sites at which nucleic acid synthesis, amplification, and/or sequencing, as discussed above, may occur. For example, each of the flow channels 222a, 222b, 222c, 222d includes three reaction sites 224 as illustrated. Many different layouts of the reaction sites may be envisaged, including regular, repeating, and non-regular patterns. For example, layouts of the reaction sites may include rectilinear (i.e., rectangular) layouts, triangular layouts, hexagonal layouts, and so forth. The particular layouts may follow the teachings of U.S. Pat. No. 7,813,013, and/or of U.S. patent application Ser. No. 13/267,565, filed on Oct. 6, 2011 which are hereby incorporated by reference in its entirety. It should be noted that the patterned substrate may also be used to control the density of the features capable of interrogation (e.g., through imaging).

Primers (e.g., P5, P7 primers) may be flowed into each of the flow channels 222a, 222b, 222c, 222d such that primers are deposited and attached to the reactions sites 224 of each of the flow channels 222a, 222b, 222c, 222d. At each reaction site 224 of each of the flow channels 222a, 222b, 222c, 222d, a nucleic acid fragment 226 may be synthesized by extension of the primers or be attached to the primers, as discussed above (phase 228). Each of the flow channels 222a, 222b, 222c, 222d generally includes a different nucleic acid fragment 226. For example, the flow channels 222a, 222b, 222c, 222d may include the nucleic acid fragments 128a, 128b, 128c, 128d of FIG. 4. In some embodiments, any of the flow channels 222a, 222b, 222c, 222d may include the same nucleic acid fragment as one or more of the other flow channels 222a, 222b, 222c, 222d.

The nucleic acid fragment 226 at each reaction site 224 of each of the flow channels 222a, 222b, 222c, 222d may be sequenced in the presence of one or more sequencing reagents 230 (phase 232). In some embodiments, amplification of the nucleic acid fragments 226 may be carried out in one or more of the flow channels 222a, 222b, 222c, 222d before the sequencing. Similarly as above, synthesis error rates and/or yields with respect to the nucleic acid fragments 226 may be obtained from the sequencing. In some embodiments, the synthesis error rates and/or the yields may be used to provide feedback to the fragment design to determine how well the fragment design was. In certain embodiments, a plurality of cycles of such feedback may be provided so that an adaptive fragment design routine may be carried out, automatically or by a user.

All or a part of the nucleic acid fragments 226 may be harvested from the substrate 221 (phase 234) based on the synthesis (or amplification) error rates and/or the yields. As illustrated, some of the nucleic acid fragments 226 (e.g., a nucleic acid fragment 236) are selectively harvested and subsequently washed out of the flow channels 222a, 222b, 222c, 222d. Other nucleic fragments 226 (e.g., a nucleic acid fragment 238) are not harvested and remain attached to the substrate 221 at the reaction sites 224. The harvesting may be based on the synthesis (or amplification) error rates and/or yields with respect to the nucleic acid fragments 226. The harvested nucleic acid fragments 226 are washed out from the flow channels 222a, 222b, 222c, 222d and may then be collected for later assembly into the synthetic polynucleotide molecule.

Figure 7:
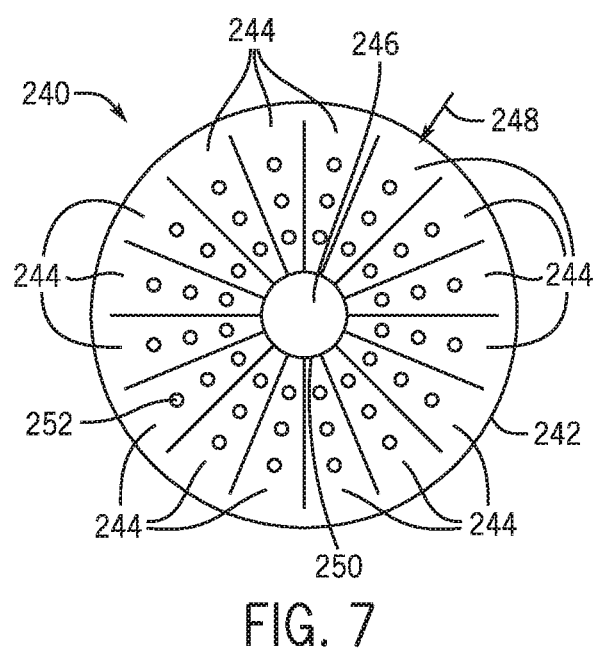
FIG. 7 is an embodiment of a microfluidic writing and reading cassette for single platform synthesis, amplification, and sequencing of a synthetic polynucleotide molecule according to embodiments of the present disclosure.

FIG. 7 illustrates an embodiment of a microfluidic writing and reading cassette 240 for single platform synthesis, amplification, and sequencing of a synthetic polynucleotide molecule according to embodiments of the present disclosure. The cassette 240 has a generally round shape as illustrated, however, many other shapes may be envisaged, including square, rectangular, triangle, hexagonal, and so forth.

The cassette 240 includes a substrate 242 and one or more flow channels 244. The flow channels 244 are next to one another and radially centered toward a central region 246. Various carrier fluids, reagents, and so forth may be introduced into (e.g., along a direction toward the central region 246 illustrated by the reference 248) the flow channels 244, and may be flowed out of the flow channels 244 (e.g., in a generally opposite direction of direction 248). Although sixteen flow channels are illustrated in FIG. 7, it is understood that the cassette 240 may include any number of flow channels (e.g., 1, 2, 3, 4, 5, 6, 7, 8, 9, 10, or more).

The central region 246 may be separated with the flow channels 244 with a rim 250. The rim 250 may be open (e.g., when installed) or closed (e.g., when removed) to allow or block carrier fluids, reagents, reactants (e.g., fragment nucleic acids), and so forth, to flow from the flow channels 244 to the central region 246. In some embodiments, the rim 250 may include a gate between the central region 246 and each of the flow channels 244. The gate may be open and closed to provide selective flow from any of the flow channels 244 to the central region 246.

Each of the flow channels 244, similar to the flow channels 222a, 222b, 222c, 222d illustrated in FIG. 6, may include on the substrate 242 one or more reaction sites 252 at which nucleic acid synthesis, amplification, and/or sequencing, as discussed above, may occur. For example, each of the flow channels 244 includes three reaction sites 252 as illustrated. The layouts of the reaction sites 252 are similar to the layouts of the reaction sites 224 of FIG. 6.

Nucleic acid synthesis, amplification, and/or sequencing may occur in the flow channels 244, similar to the flow channels 222a, 222b, 222c, 222d as described in FIG. 6. Different from the flow cell 220 of FIG. 6, however, the cassette 240 includes the central region 246 that may be used for assembly and repair of nucleic acid fragments, such as those described in phase 32 of FIG. 1 and phases 142, 148, 156 of FIG. 4. In addition, the central region 246 may also be used for assembly quality control, such as that described in phase 36 of FIG. 1 and phase 158 of FIG. 4. Moreover, the assembled polynucleotide (e.g., from the nucleic acid fragments) may be harvested from the central region 246.

Figure 8:
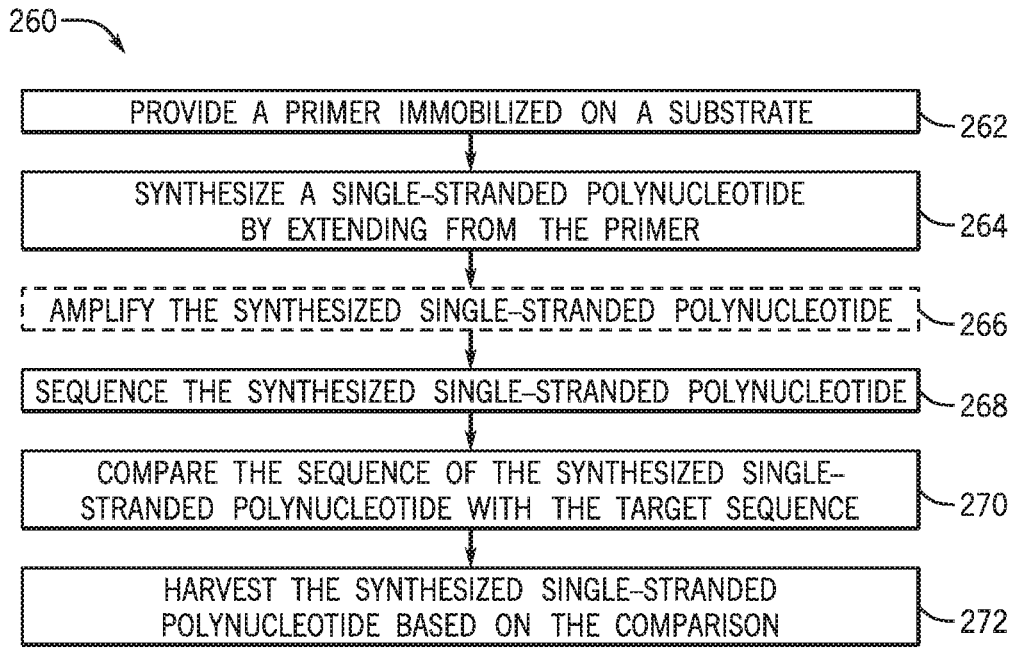
FIG. 8 is a flow diagram of a technique for generating a template-independent polynucleotide fragment of a synthetic polynucleotide molecule with sequencing feedback according to embodiments of the present disclosure.

FIG. 8 illustrates a flow diagram of a technique 260 for generating a template-independent polynucleotide fragment of a synthetic polynucleotide molecule with sequencing feedback according to embodiments of the present disclosure. The technique 260 may start with providing a primer immobilized on a substrate (block 262). Synthesis of a single-stranded polynucleotide may be carried out by extension of the primer (block 264). The synthesis of the single-stranded polynucleotide may be based on a target nucleic acid sequence.

In some embodiments, the synthesized single-stranded polynucleotide may be amplified (block 266) using any suitable methods as discussed above. In other embodiments, such amplification is optional, and accordingly, the block 266 is illustrated with a dashed box.

The synthesized single-stranded polynucleotide may then be sequenced (block 268). The sequence of the single-stranded polynucleotide may be compared with the target nucleic acid sequence (block 270) for synthesis quality control. As discussed above, synthesis (or amplification) error rates and/or yields may be used for quality control. For example, synthesis (or amplification) error rates and/or yields may be used to provide feedback to the fragment design to determine design quality. Based on the sequence comparison (e.g., synthesis error rates and/or yields), the synthesized single-stranded polynucleotide may then be harvested (block 272).

Figure 9:
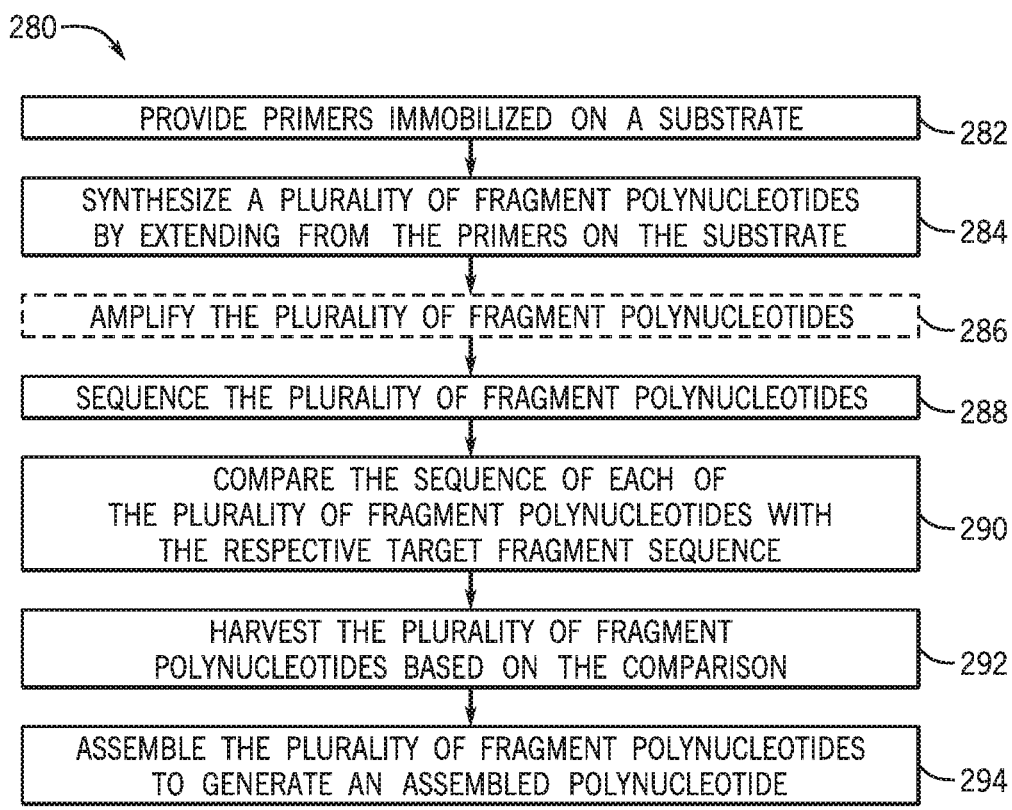
FIG. 9 is a flow diagram of a technique for generating an assembled synthetic polynucleotide molecule with sequencing feedback according to embodiments of the present disclosure.

FIG. 9 illustrates a flow diagram of a technique 280 for generating an assembled synthetic polynucleotide molecule with sequencing feedback according to embodiments of the present disclosure. The technique 280 may start with providing primers immobilized on a substrate (block 282). Based on a target nucleic acid sequence, a plurality of nucleic acid fragments may be designed. Each of the designed nucleic acid fragments may be synthesized, amplified, sequenced, and/or harvested according to the technique 260 described in FIG. 8.

Based on sequences of the designed nucleic acid fragments, a plurality of fragment polynucleotides may be synthesized by extension of the primers on the substrate (block 284). In some embodiments, the plurality of fragment polynucleotides may be amplified (block 286) using any suitable methods as discussed above. In other embodiments, such amplification is optional, and accordingly, the block 286 is illustrated with a dashed box.

The plurality of fragment polynucleotides may then be sequenced (block 288). The sequence of each of the plurality of fragment polynucleotides may be compared with the sequence of its respective designed nucleic acid fragment (block 290) for synthesis quality control. As discussed above, synthesis (or amplification) error rates and/or yields may be used for quality control. For example, synthesis (or amplification) error rates and/or yields may be used to provide feedback to the fragment design to determine design quality.

Based on the sequence comparison (e.g., synthesis (or amplification) error rates and/or yields), the plurality of fragment polynucleotides may then be harvested (block 292). The harvested plurality of fragment polynucleotides may be further assembled and/or repaired to generate an assembled polynucleotide (block 294). In addition, as discussed above, quality control (e.g., sequencing) may be carried out to the assembled polynucleotide. The quality control may provide feedback to the fragment design and may be used for harvesting the assembled polynucleotide.

Figure 10:
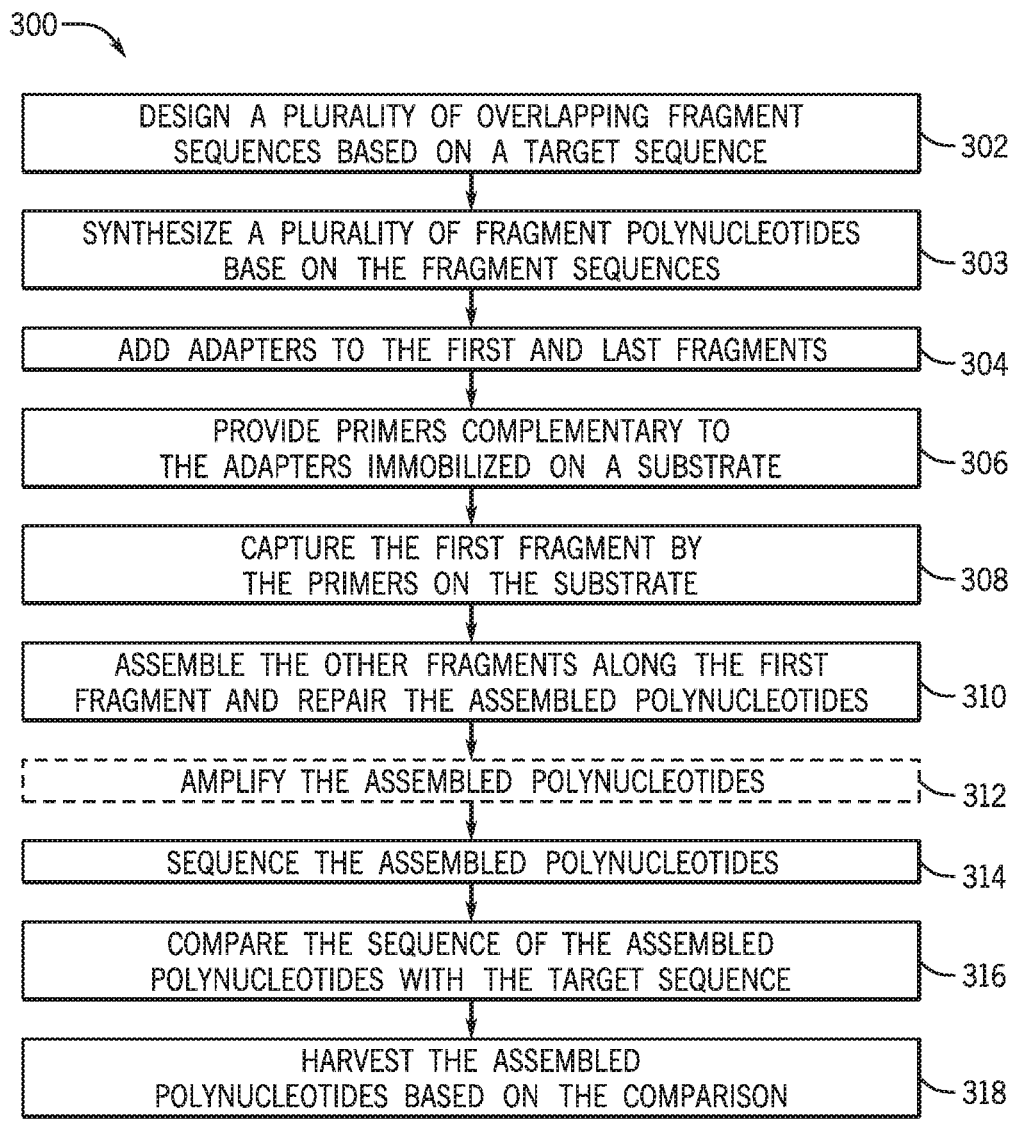
FIG. 10 is a flow diagram of a quality feedback technique for synthetic polynucleotide design based on sequencing feedback from the assembled synthetic polynucleotide according to embodiments of the present disclosure.

FIG. 10 illustrates a flow diagram of a quality feedback technique 300 for synthetic polynucleotide design based on sequencing feedback from the assembled synthetic polynucleotide according to embodiments of the present disclosure. The technique 300 may start with the system (e.g., system 50) receiving a plurality of overlapping fragment sequences based on a target sequence (block 302). The designed fragment sequences may be designed by an operator or may be designed automatically by the system according to a rules-based technique that may update according to received quality information as provided herein. For example, a target sequence may include a nucleotide sequence that is associated with a poor fragmenting score. That is, previous sequencing data for other target sequences may indicate that a fragment designed to break within that sequence may be associated with an assembled molecule with a high error rate (or a low fragment yield). Further, other nucleotide sequences may be associated with high fragmenting scores. In such embodiments, an automatic rules-based system may prefer to create fragments that break within higher fragmenting score regions relative to lower fragmenting score regions of the target sequence.

Based on the designed fragment sequences, a plurality of fragment polynucleotides may be synthesized (block 303). Each of the plurality of fragment polynucleotides may be synthesized with any suitable methods, including methods described in FIG. 8. The first and last fragment polynucleotides may be further modified with adapters (block 304). For example, one adapter may be ligated to the 5' end of the first polynucleotide, and another adapter may be ligated to the 3' end of the last polynucleotide.

Primers that are complementary to the adapters may be immobilized on a substrate (block 306). As such, the first fragment polynucleotides may be captured by the primers on the substrate (block 308). Other fragment polynucleotides may be flowed on the substrate such that the other fragment polynucleotides are assembled along the first fragment polynucleotides, and the assembled polynucleotides are further repaired (block 310).

In some embodiments, the assembled polynucleotides may be amplified (block 312) using any suitable methods as discussed above. In other embodiments, such amplification is optional, and accordingly, the block 312 is illustrated with a dashed box.

The assembled polynucleotides may then be sequenced (block 314). The sequence of the assembled polynucleotides may be compared with the target sequence (block 316) for synthesis quality control. As discussed above, synthesis error rates and/or yields may be used for quality control. For example, synthesis error rates and/or yields may be used to provide feedback to the fragment design (provided at block 302) to determine the fragment design quality and/or the overall quality of the synthetic nucleic acid molecule. Based on the sequence comparison (e.g., synthesis (or amplification) error rates and/or yields), the assembled polynucleotides may then be harvested (block 318).

While only certain features of the contemplated embodiments have been illustrated and described herein, many modifications and changes will occur to those skilled in the art. Further, it should be understood that certain elements of the disclosed embodiments may be combined or exchanged with one another. It is, therefore, to be understood that the appended claims are intended to cover all such modifications and changes as fall within the true spirit of the disclosure.

What is claimed is:

1. A system for synthesizing a nucleic acid, comprising:
(a) a synthesis substrate comprising a plurality of flow channels, each of the plurality of flow channels (i) comprising a plurality of immobilized primer oligonucleotides and (ii) lacking a template nucleic acid complementary to the plurality of immobilized primer oligonucleotides;
(b) a processor-based device storing executable instructions and coupled to the synthesis substrate, wherein the executable instructions are configured to:
(i) receive one or more synthesis signals for each respective flow channel indicative of a presence of a first polymerase extending de novo the plurality of immobilized primer oligonucleotides in the absence of the template nucleic acid to generate a respective plurality of single-stranded fragment polynucleotides based on one of a plurality of target sequences;
(ii) control entry of a first sequencing reagent, a second sequencing reagent, and a second polymerase into the flow channels based on the one or more synthesis signals, wherein the first sequencing reagent comprises one or more nucleotide monomers, wherein the one or more nucleotide monomers form a plurality of polynucleotides complementary to at least a portion of the plurality of fragment polynucleotides, wherein the second sequencing reagent comprises at least one nucleotide monomer, and wherein the at least one nucleotide monomer of the second sequencing reagent comprises a reversibly terminating moiety;
iii) receive one or more sequencing signals for each respective flow channel indicative of a presence of the first sequencing reagent and the second sequencing reagent in the presence of the second polymerase;
(iv) determine a sequence of each of the plurality of fragment polynucleotides based on the one or more sequencing signals; and
(v) provide an indication related to a comparison of the sequence of each of the plurality of fragment polynucleotides with the respective target sequence;

(c) an assembly cell comprising an assembly substrate comprising an immobilized anchor oligonucleotide, wherein the assembly cell is configured to gather each of the plurality of fragment polynucleotides from each of the plurality of flow channels and assemble each of the plurality of fragment polynucleotides to generate an assembled polynucleotide; and (d) the assembled polynucleotide, wherein the assembled polynucleotide comprises double-stranded regions and single-stranded gaps regions, wherein the single-stranded regions are in both strands, and wherein the assembled polynucleotide is immobilized on the assembly substrate via the immobilized anchor oligonucleotide.

2. The system of claim 1, wherein each of the plurality of flow channels is configured to immobilize a plurality of amplification oligonucleotides on the synthesis substrate, and wherein the executable instructions further comprise instructions to amplify the plurality of fragment polynucleotides by annealing the fragment polynucleotides to one or more of the plurality of immobilized amplification oligonucleotides.

3. The system of claim 1, wherein the executable instructions further comprise instructions to amplify the assembled polynucleotide by annealing to one or more of a plurality of immobilized amplification oligonucleotides in the assembly cell.

4. The system of claim 1, wherein the executable instructions further comprise instructions to receive a third sequencing reagent at the assembly cell in the presence of a third polymerase and to receive a fourth sequencing reagent, wherein the third sequencing reagent comprises one or more nucleotide monomers, wherein the one or more nucleotide monomers form a plurality of polynucleotides complementary to at least a portion of the assembled polynucleotide, wherein the fourth sequencing reagent comprises at least one nucleotide monomer, wherein the at least one nucleotide monomer of the fourth sequencing reagent comprises a reversibly terminating moiety, and wherein the fourth sequencing reagent is provided subsequent to providing the third sequencing reagent, whereby sequence information for the assembled polynucleotide is obtained.

5. The system of claim 1, wherein the executable instructions further comprise instructions to harvest the plurality of fragment polynucleotides if the sequence of each of the plurality of fragment polynucleotides is identified to include the respective target sequence or to be complementary to the respective target sequence.

6. The system of claim 5, wherein the executable instructions further comprise instructions to harvest the plurality of fragment polynucleotides if the sequence of each of the plurality of fragment polynucleotides has a sequence error rate less than a predetermined threshold.

7. The system of claim 1, wherein the executable instructions further comprise instructions to harvest the plurality of fragment polynucleotides by cleaving the plurality of fragment polynucleotides from the plurality of primer oligonucleotides.

8. The system of claim 1, comprising a processor configured to generate a sequence accuracy score or metric for each of the plurality of fragment polynucleotides.

9. The system of claim 1, wherein the first polymerase comprises terminal deoxynucleotidyl transferase (TdT).

10. The system of claim 1, wherein the synthesis substrate comprises a bead, a magnetic bead, a glass slide, a microchip, a nano droplet, an electrowetting cartridge, or any combination thereof.

11. The system of claim 1, wherein the plurality of immobilized primer oligonucleotides comprises a cleavable linker.

12. The system of claim 1, wherein the respective plurality of single-stranded fragment polynucleotides based on one of a plurality of target sequences comprises a plurality of overlapping nucleic acid fragments having complementary portions to at least one other fragment of the nucleic acid fragments.

13. The system of claim 12, wherein the plurality of immobilized primer oligonucleotides further comprises the respective plurality of single-stranded fragment polynucleotides based on one of a plurality of target sequences.

14. The system of claim 12, wherein the assembly cell further comprises the respective plurality of single-stranded fragment polynucleotides based on one of a plurality of target sequences.

15. The system of claim 12, wherein the plurality of target sequences comprises a first end sequence, a second end sequence, and an intermediate sequence therebetween, wherein the plurality of overlapping nucleic acid fragments comprises a first fragment comprising a portion having the first end sequence, and wherein the assembled polynucleotide is immobilized on the assembly substrate via hybridization of the first fragment with the immobilized anchor oligonucleotide.

16. The system of claim 15, wherein an end of the first fragment comprises a cleavable adapter.

17. The system of claim 1, wherein the assembly substrate comprises a plurality of immobilized amplification oligonucleotides.

18. The system of claim 17, further comprising a solution in contact with the assembly substrate, wherein the solution comprises reagents suitable for performing bridge amplification.

19. The system of claim 1, further comprising a solution in contact with the assembly substrate, wherein the solution comprises reagents suitable for gap repair.

20. A system for synthesizing a nucleic acid, comprising:
(a) a synthesis substrate comprising a plurality of flow channels, each of the plurality of flow channels (i) comprising a plurality of immobilized primer oligonucleotides and (ii) lacking a template nucleic acid complementary to the plurality of immobilized primer oligonucleotides;
(b) a processor-based device storing executable instructions and coupled to the synthesis substrate, wherein the executable instructions are configured to:
(i) receive one or more synthesis signals for each respective flow channel indicative of a presence of a first polymerase extending de novo the plurality of immobilized primer oligonucleotides in the absence of the template nucleic acid to generate a respective plurality of single-stranded fragment polynucleotides based on one of a plurality of target sequences, wherein the first polymerase comprises terminal deoxynucleotidyl transferase (TdT);
(ii) control entry of a first sequencing reagent, a second sequencing reagent, and a second polymerase into the flow channels based on the one or more synthesis signals, wherein the first sequencing reagent comprises one or more nucleotide monomers, wherein the one or more nucleotide monomers form a plurality of polynucleotides complementary to at least a portion of the plurality of fragment polynucleotides, wherein the second sequencing reagent comprises at least one nucleotide monomer, and wherein the at least one nucleotide monomer of the second sequencing reagent comprises a reversibly terminating moiety;

(iii) receive one or more sequencing signals for each respective flow channel indicative of a presence of the first sequencing reagent and the second sequencing reagent in the presence of the second polymerase;

(iv) determine a sequence of each of the plurality of fragment polynucleotides based on the one or more sequencing signals; and (v) provide an indication related to a comparison of the sequence of each of the plurality of fragment polynucleotides with the respective target sequence;

(c) a processor configured to generate a sequence accuracy score or metric for each of the plurality of fragment polynucleotides;

(d) an assembly cell comprising an assembly substrate comprising an immobilized anchor oligonucleotide, wherein the assembly cell is configured to gather each of the plurality of fragment polynucleotides from each of the plurality of flow channels and assemble each of the plurality of fragment polynucleotides to generate an assembled polynucleotide; and (e) the assembled polynucleotide, wherein the assembled polynucleotide comprises double-stranded regions and single-stranded regions, wherein the single-stranded regions are in both strands, and wherein the assembled polynucleotide is immobilized on the assembly substrate via the immobilized anchor oligonucleotide.

* * * * *